(12) United States Patent
Chafin et al.

(10) Patent No.: US 12,216,089 B2
(45) Date of Patent: *Feb. 4, 2025

(54) PROCESSING SYSTEM FOR PROCESSING SPECIMENS USING ACOUSTIC ENERGY

(71) Applicant: Ventana Medical Systems, Inc., Tucson, AZ (US)

(72) Inventors: David Chafin, Tucson, AZ (US); Michael Otter, Tucson, AZ (US); Abbey Pierson, Tucson, AZ (US); Jefferson Curtis Taft, Sahuarita, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/107,951

(22) Filed: Feb. 9, 2023

(65) Prior Publication Data

US 2023/0184721 A1 Jun. 15, 2023

Related U.S. Application Data

(63) Continuation of application No. 16/287,827, filed on Feb. 27, 2019, now Pat. No. 11,614,426, which is a continuation of application No. 13/582,705, filed as application No. PCT/US2011/027284 on Mar. 4, 2011, now Pat. No. 10,267,769.

(60) Provisional application No. 61/310,653, filed on Mar. 4, 2010.

(51) Int. Cl.
| | | |
|---|---|---|
| *G01N 29/07* | (2006.01) | |
| *G01N 1/30* | (2006.01) | |
| *G01N 29/024* | (2006.01) | |
| *G01N 29/44* | (2006.01) | |
| *G01N 33/483* | (2006.01) | |

(52) U.S. Cl.
CPC ............... *G01N 29/07* (2013.01); *G01N 1/30* (2013.01); *G01N 29/024* (2013.01); *G01N 29/4427* (2013.01); *G01N 33/4833* (2013.01); *G01N 2291/02466* (2013.01); *G01N 2291/02475* (2013.01)

(58) Field of Classification Search
None
See application file for complete search history.

(56) References Cited

U.S. PATENT DOCUMENTS

| | | | |
|---|---|---|---|
| 10,267,769 B2 * | 4/2019 | Otter | G01N 29/024 |
| 11,614,426 B2 * | 3/2023 | Chafin | G01N 1/30 |
| | | | 435/40.5 |

* cited by examiner

*Primary Examiner* — Blaine Lankford
(74) *Attorney, Agent, or Firm* — Charney IP Law LLC; Thomas M. Finetti

(57) ABSTRACT

A method for fixing a biological sample includes delivering energy through a biological sample that has been removed from a subject, while fixing the biological sample. A change in speed of the energy traveling through the biological sample is evaluated to monitor the progress of the fixation. A system for performing the method can include a transmitter that outputs the energy and a receiver configured to detect the transmitted energy. A computing device can evaluate the speed of the energy based on signals from the receiver.

15 Claims, 24 Drawing Sheets

PROCESSING SYSTEM FOR PROCESSING SPECIMENS USING ACOUSTIC ENERGY

CROSS-REFERENCE TO RELATED APPLICATION

This application is a continuation of U.S. patent application Ser. No. 16/287,827 filed on Feb. 27, 2019, which application is a continuation of U.S. patent application Ser. No. 13/582,705 filed on Sep. 4, 2012, which claims the benefit of the filing date of International Application No. PCT/US2011/027284 filed on Mar. 4, 2011 and which application claims the benefit of the filing date of U.S. Provisional Patent Application No. 61/310,653 filed on Mar. 4, 2010, the disclosures of which are hereby incorporated by reference herein in their entireties.

BACKGROUND

Technical Field

The present invention relates generally to methods and systems for analyzing specimens using energy. More specifically, the invention is related to methods and systems for analyzing tissue specimens using acoustic energy.

Description of the Related Art

Preservation of tissues from surgical procedures is currently a topic of great importance. Currently, there are no standard procedures for fixing tissues and this lack of organization leads to a variety of staining issues both with primary and advanced stains. The first step after removal of a tissue sample from a subject is to place the sample in a liquid that will suspend the metabolic activities of the cells. This process is commonly referred to as "fixation" and can be accomplished by several different types of liquids. The most common fixative in use by anatomical pathology labs is 10% neutral buffered formalin (NBF). This fixative forms cross-links between formaldehyde molecules and amine containing cellular molecules. In addition, this type of fixative preserves proteins for storage.

Another type of common fixative is ethanol or solvent based solutions. These fixatives tend to dehydrate the tissue and are commonly termed "precipitive fixatives." As the term suggests, these solutions tend to denature proteins and inactivate cellular constituents in a manner different from formalin.

Biological samples that are "fixed" in 10% neutral buffered formalin preserve the tissue from autocatalytic destruction by cross-linking much of the protein and nucleic acids via methylene bridges. The cross-linking preserves the characteristics of the tissue, such as the tissue structure, cell structure and molecular integrity. Typically, fixation with 10% NBF takes several hours and can be thought of as two separate steps. First is the diffusion step where a large volume of formalin on the outside of the tissue needs to diffuse into the tissue. This process is governed by the laws of physics and depends on the tissue thickness, concentration of formalin and temperature (e.g., formalin temperature, tissue temperature, etc.). In the second step, the formalin molecules interact with biological molecules in the tissue, becoming incorporated into the methylene cross-links. This cross-link structure can keep the cellular structure intact during subsequent processing such as tissue dehydration and embedding the tissue into paraffin wax.

If the tissue is over-fixed, it may be difficult to diffuse processing liquids through the tissue due to the extensive network of cross-linked molecules. This can result in inadequate penetration of the processing liquids. If the processing liquid is a stain, slow diffusion rates can cause uneven and inconsistent staining. These types of problems can be increased if the stain has relatively large molecules. For example, conjugated biomolecules (antibody or DNA probe molecules) can be relatively large, often having a mass of several hundred kilodaltons, causing them to diffuse slowly into solid tissue with typical times for sufficient diffusion being in a range of several minutes to a few hours.

If the tissue is under-fixed, the tissue may be susceptible to severe morphology problems or autocatalytic destruction. Severe morphology problems result from an incomplete network of cross-linked molecules and subsequent shrinking of cells, nuclei and cytoplasm during dehydration steps. Autocatalytic destruction can result in loss of tissue structure, cell structure and tissue morphology, especially if the tissue is not processed within a relatively short period of time. Accordingly, under-fixed tissue may be unsuitable for examination and is often discarded.

To prepare biological samples for examination, tissues are often stained by using a variety of dyes, immunohistochemical (IHC) staining processes, or in situ hybridization (ISH). The rate of immunohistochemical and in situ hybridization staining of fixed tissue (e.g., paraffin embedded sectioned fixed tissue) on a microscope slide is limited by the speed at which molecules (e.g., conjugating biomolecules) can diffuse into the fixed tissue and interact molecularly from an aqueous solution placed in direct contact with the tissue section. In some tissues, such as relatively fatty tissue (e.g., breast tissue), it is difficult to predict fixation processing times due to these inaccessibility issues. Accordingly, tissues can be over-fixed (e.g., excessively cross-linked) or under-fixed (e.g., insufficiently cross-linked).

A wide variety of techniques can be used to analyze biological samples either prior to or after exposure to a fixative. Example techniques include microscopy, microarray analyses (e.g., protein and nucleic acid microarray analyses), mass spectrometric methods and a variety of molecular biology techniques. However, there are no suitable methods to determine the fixation state of a sample.

Conventional pathology practice is often based on predetermined fixation settings based on empirical knowledge of processing times for sample dimensions (e.g., thicknesses) and tissue type. It is often difficult to stain tissue without knowing this information; tissue is thus often tested to obtain such information. Unfortunately, the testing may be time-consuming, destroy significant portions of sample, and lead to reagent waste. By way of example, numerous iterations with different antigen retrieval settings for IHC/ISH stains may be performed in order to match and/or compensate for an unknown fixation state and an unknown tissue composition. The repeated staining runs result in additional sample material consumption and lengthy periods for diagnosis.

Acoustical energy has been used in a number of applications in science and medicine. These include attempts to speed up biological reactions ranging from assays that have molecular interactions to fixation of tissue samples. In addition, acoustics have long been used to monitor for the presence of submarines and other maritime vessels by the US navy. Acoustics have also been applied in monitoring ocean temperatures by measuring the speed of a signal between two points. Unfortunately, acoustics have not been used to determine desired characteristics of specimens.

BRIEF SUMMARY

At least some embodiments are directed to methods and systems for analyzing a specimen. The specimen can be analyzed based on its properties. These properties include acoustic properties, mechanical properties, optical properties, or the like that may be static or dynamic during processing. In some embodiments, the properties of the specimen are continuously or periodically monitored during processing to evaluate the state and condition of the specimen. Based on obtained information, processing can be controlled to enhance processing consistency, reduce processing times, improve processing quality, or the like.

Acoustics can be used to analyze soft objects, such as tissue samples. When an acoustical signal interacts with tissue, the transmitted signal depends on several mechanical properties of the sample, such as elasticity and firmness. As tissue samples that have been placed into fixative (e.g., formalin) become more heavily cross-linked, the speed of transmission will change according to the properties of the tissue.

In some embodiments, a status of a biological sample can be monitored based on a time of flight of acoustic waves. The status can be a density status, fixation status, staining status, or the like. Monitoring can include, without limitation, measuring changes in sample density, cross-linking, decalcification, stain coloration, or the like. The biological sample can be non-fluidic tissue, such as bone, or other type of tissue.

In some embodiments, methods and systems are directed to using acoustic energy to monitor a specimen. Based on interaction between the acoustic energy in reflected and/or transmission modes, information about the specimen may be obtained. Acoustic measurements can be taken. Examples of measurements include acoustic signal amplitude, attenuation, scatter, absorption, time of flight (TOF) in the specimen, phase shifts of acoustic waves, or combinations thereof.

The specimen, in some embodiments, has properties that change during processing. In some embodiments, a fixative is applied to the specimen. As the specimen becomes more fixed, mechanical properties (e.g., elasticity, stiffness, etc.) change due to molecular cross-linking. These changes can be monitored using sound speed measurements via TOF. Based on the measurements, a fixative state or other histological state of the specimen can be determined. To avoid under-fixation or over-fixation, the static characteristics of the tissue, dynamic characteristics of the tissue, or both can be monitored. Characteristics of the tissue include transmission characteristics, reflectance characteristics, absorption characteristics, attenuation characteristics, or the like.

In some embodiments, a method for processing a tissue sample includes performing a process (for example, a fixation process or other histological process, such as embedding, dehydrating, infiltrating, embedding, sectioning, and/or staining) on a tissue sample that has been removed from a subject to at least partially fixes or otherwise alters the tissue sample. In certain embodiments, acoustic waves are transmitted through the tissue sample while performing the fixation process. A change in speed of at least some of the transmitted acoustic waves that travel through the tissue sample are evaluated after performing at least a portion of the process. In certain embodiments, most of the acoustic waves transmitted through the specimen are evaluated.

To evaluate the change in speed of the acoustic waves, the acoustic waves before entering the tissue sample are compared to the acoustic waves that have exited the tissue sample. In some embodiments, a TOF is determined based on the comparison. In some embodiments, the TOF of fixation media in which the sample is submerged may be measured and used to determine the TOF in the sample. In certain embodiments, the TOF is measured and recorded prior to insertion of the sample, to evaluate temperature effects of the media. Data from such measurements can be stored for later reference. Sound speeds in the sample are evaluated based on one or more of a TOF of the media, a TOF of a measuring channel, or other TOF measurements that can be used to determine secondary effects, such as temperature effects.

In some embodiments, a tissue processing protocol is generated based on an evaluation of the change in speed of the acoustic signal applied to the tissue sample. The tissue processing protocol can be used, either manually or in an automated system, to process the specimen and can include a fixating protocol, a tissue preparation protocol, an embedding protocol, and/or a staining protocol. In certain embodiments, the fixation protocol can include length of fixation time, temperature of the fixative, or temperature of the specimen. The tissue preparation protocol can include instructions for the number and types of liquids to be applied to the specimen to prepare the specimen for embedding. The liquids can include clearing agents, infiltration agents, dehydration agents, or the like. In certain embodiments, the embedding protocol includes the type and composition of material in which the specimen is to be embedded. The staining protocol can include a number and types of reagents, reagent compositions, reagent volumes, processing times, instructions for an automated staining unit, or the like. Other types of protocols can also be generated. In an automated system, a controller can use the protocol to process the specimens.

The specimen can be processed based on the evaluation of the change in speed of the acoustic waves. In certain embodiments, the fixation process is stopped based on the evaluation. In certain embodiments the staining process is controlled based on the evaluation. In yet other embodiments, an embedding process is performed based on the evaluation.

In some embodiments, a method for fixing a tissue sample includes performing a fixation process on a tissue sample that has been removed from a subject to at least partially fix the tissue sample. Acoustic waves are transmitted through at least a portion of the tissue sample while performing the fixation process. A change in speed of at least some of the acoustic waves that travel through the portion of the tissue sample is evaluated. In certain embodiments, the level of fixation is monitored after performing at least a portion of the fixation process.

In other embodiments, a method comprises performing a fixation process on a plurality of tissue samples. At least one sound speed characteristic is obtained for each of the tissue samples. The sound speed characteristics are correlated to the respective tissue samples. The correlated sound speed characteristics are stored by a computing device. In some embodiments, the correlated sound speed characteristics are stored in memory or in a database. A tissue specimen can be processed based on at least one of the stored sound speed characteristics. The processing can include at least one of a fixation process, a tissue preparation process, an embedding process, and a staining process.

In certain embodiments, a method for evaluating a tissue sample includes analyzing acoustic wave speed before, during and/or after sample processing. This is accomplished by first establishing a baseline measurement for a fresh, unfixed tissue sample by delivering an acoustic wave from a transmitter to the tissue sample taken from a subject. The baseline TOF acoustic wave is detected using a receiver. After or during processing the tissue sample, a second acoustic wave is delivered from the transmitter to the tissue sample. The second TOF acoustic wave is detected using the receiver after the second acoustic wave has traveled through the tissue sample. Sound speeds in the tissue sample are compared based on the first TOF and the second TOF to determine a change in speed. These measurements can be unique for each tissue sample analyzed and therefore used to establish a baseline for each tissue sample. Additional TOF measurements can be used to determine TOF contributions attributable to the media, measurement channel, or the like. In some embodiments, the TOF of the media is measured when no specimen is present to determine a baseline TOF of the media.

In certain embodiments, a fixation process is performed on a tissue sample to fix at least a portion of the tissue sample. A change in speed of sound traveling through the tissue sample is evaluated using acoustic waves that have traveled through at least a portion of the tissue sample. The fixation process is adjusted based on the evaluation of the change of the speed of sound. In certain embodiments, adjusting of the fixation process includes reducing fixation time, adjusting the composition of the fixative, changing a temperature of the fixative, or combinations thereof.

A system for evaluating a tissue sample includes a transmitter, a receiver, and a computing device. The transmitter is configured to output acoustic energy through a tissue sample that has been taken from a subject. The receiver is configured to detect the acoustic energy that has traveled through the tissue sample before, during or after a fixation protocol has been administered. The computing device is able to receive data from the transmitter and the receiver. The computing device is configured to evaluate the speed of sound data and convert the received data into a TOF value.

In some embodiments, a system for monitoring a tissue sample includes a container, a transmitter, a receiver, and a computing device. The transmitter is configured to output acoustic waves through a tissue specimen located in a chamber of the container in response to a drive signal. The receiver is positioned to detect acoustic waves transmitted through the tissue specimen. The receiver is also configured to output a signal. In certain embodiments, the receiver is positioned to detect acoustic waves that have traveled across the thickness of the tissue specimen. In other embodiments, the receiver is positioned to detect acoustic waves that are reflected from the tissue specimen. The system can include a transducer that includes both the transmitter and the receiver (pulser/receiver combination) alternating electronically between transmission and reception mode.

The computing device is coupled to the transmitter and is configured to evaluate sound speeds in the tissue sample by comparing TOF changes. In some embodiments, the computing device includes memory that stores information about the tissue specimen. The computing device is capable of using the evaluation of the sound speeds in the tissue sample and the stored information to determine information about the tissue sample.

In yet other embodiments, a method of analyzing a tissue sample includes transmitting acoustic energy through at least a portion of the tissue sample. A comparative TOF of the acoustic energy in the tissue sample is determined. A degree of fixation, if any, of the tissue sample based on the comparative TOF of the acoustic energy is determined. The sample can be analyzed during a fixation protocol, which is either continued or the tissue sample is moved to a different process depending on the relative state of fixation (e.g., if a desired or target degree of fixation is reached). In certain embodiments, a desired degree of fixation can be in a range of degrees of fixation. In other embodiments, the desired degree of fixation is a threshold amount of fixation that can be specified by, for example, a user.

The tissue sample is moved to the next process (e.g., from a fixation to another process) when the degree of change of the TOF signal indicates minimal changes in fixation have occurred, for example, in a certain period of time. In certain embodiments, evaluating the degree of fixation includes comparing the TOF to a reference TOF. The reference TOF can be stored by a computing device, determined using TOF measurements of the tissue sample, or combinations thereof. In other embodiments, evaluating the degree of fixation includes evaluating a change in the speed of sound in the tissue sample to a reference change in the speed of sound. The degree of fixation is at or above the desired degree of fixation when the change of sound speed is less than the reference change of sound speed. The reference change of sound speed can be a calculated reference change of sound speed, a measured change of sound speed of a similar tissue type, or combinations thereof. For example, calculated and measured change of sound speeds can be used to determine the reference change.

In yet other embodiments, a method for fixing a tissue sample that has been removed from a subject includes contacting the tissue sample with a liquid fixative to at least partially fix the tissue sample. Acoustic waves are transmitted through at least a portion of the tissue sample while the liquid fixative at least partially fixes the tissue sample. Changes in speed of at least some of the acoustic waves that travel through the portion of the tissue sample are evaluated. In certain embodiments, the changes in speed are due to the liquid fixative fixing the tissue sample.

The tissue sample can be an unfixed tissue sample (e.g., a freshly cut tissue sample) that is brought into contact with the liquid fixative. The changes in the speed of sound can be evaluated continuously or intermittently throughout the entire fixation process or a portion of the fixation process. Once the tissue sample is properly fixed, the tissue sample is removed from the liquid fixative. In certain embodiments, the tissue sample is submerged in a bath of the liquid fixative. The fixation process can be stopped by removing the tissue sample from the bath.

The acoustic waves can be transmitted through the tissue sample as the liquid fixative changes the degree of fixation of the tissue sample. The evaluation of the change in speed can be used to monitor the degree of fixation of the tissue sample. After the tissue sample is fixed, characteristics of the tissue sample can be evaluated to monitor the state of the tissue sample, even after long term storage.

In certain embodiments, a tissue sample is evaluated using sound waves while the tissue sample is submerged in a liquid fixative. The tissue sample is pulled out of a bath of liquid fixative based on the degree of fixation of the tissue sample. The degree of fixation can be set by a user or can be automatically determined by a controller. The tissue sample can then be rinsed and further processed.

Samples can be monitored based on TOF. A change in speed of acoustic waves that travel through the sample can be used to obtain information about the sample. One or more compensation algorithms, smoothing algorithms, comparison protocols (e.g., phase angle difference routines), interactive algorithms, predictive modeling or algorithms, signal processing algorithms, combinations thereof, or other algorithms or protocols can be used to monitor the sample. In certain embodiments, signals with different characteristics (e.g., waveforms, frequencies, number of bursts, or the like) can be used to monitor the sample. Signals and corresponding measured data can be used to determine time delays, time shifts, or other changes using the signals. Different signals can be used to obtain different data or measurements, such as change in phases.

In some embodiments, a method comprises performing a process on a tissue sample that has been removed from a subject to alter the tissue sample. Acoustic waves are transmitted through at least a portion of the tissue sample. Measuring or monitoring change in speed of at least some of the acoustic waves that travel through the portion of the tissue sample after performing at least a portion of the process. In various embodiments, the process includes fixating, cross-linking, perfusing of fluids with different characteristics (e.g., densities), thermal changes, decalcification, and/or dehydration. In certain embodiments, the density properties of the tissue are monitored during a reaction that alters the sample density. A wide range of histological processes, including, without limitation, a fixation process, a dehydration process, an embedding, a staining process, etc., can be monitored or analyzed.

BRIEF DESCRIPTION OF THE SEVERAL VIEWS OF THE DRAWINGS

Non-limiting and non-exhaustive embodiments are described with reference to the following drawings. The same reference numerals refer to like parts or acts throughout the various views, unless otherwise specified.

DETAILED DESCRIPTION

Figure 1:
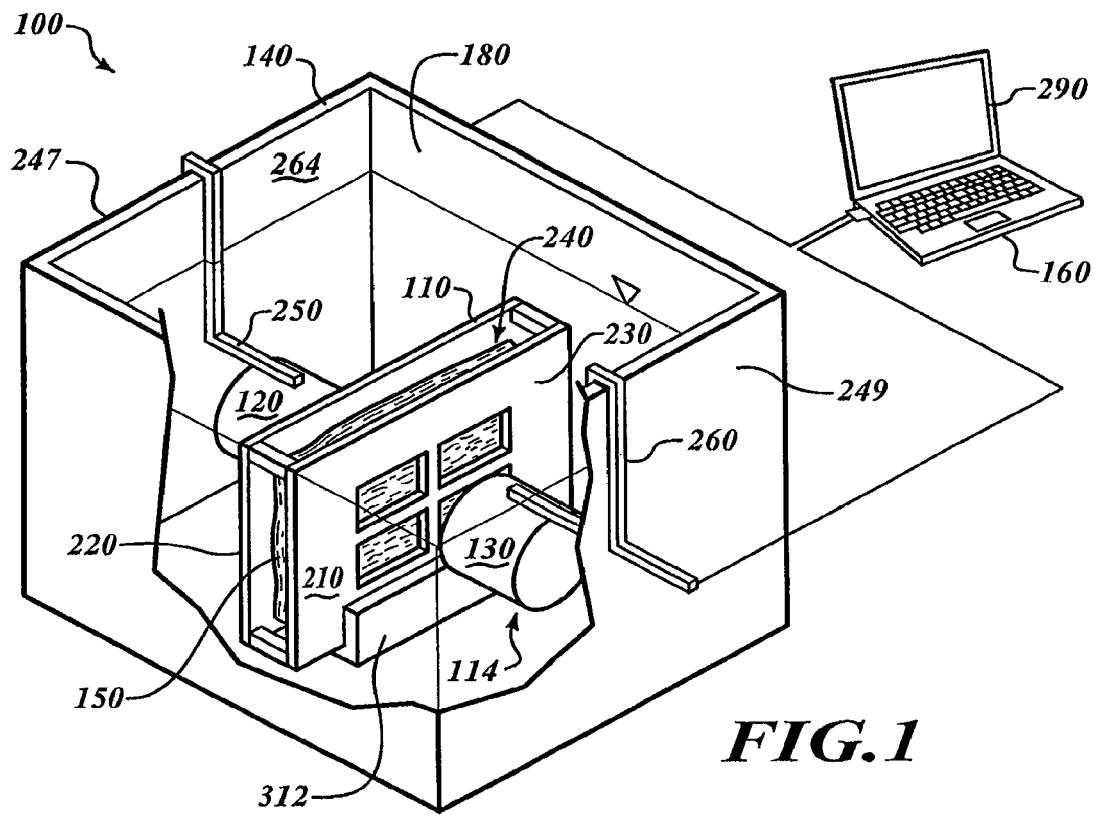
FIG. 1 is an isometric, cutaway view of a processing system containing a specimen holder with a specimen, in accordance with one embodiment.

FIG. 1 shows a processing system 100 for processing specimens. The processing system 100 includes a specimen holder 110, a container 140, and an analyzer 114 positioned in the container 140. The analyzer 114 includes a transmitter 120 and a receiver 130. A computing device 160 is communicatively coupled to the analyzer 114.

Figure 2:
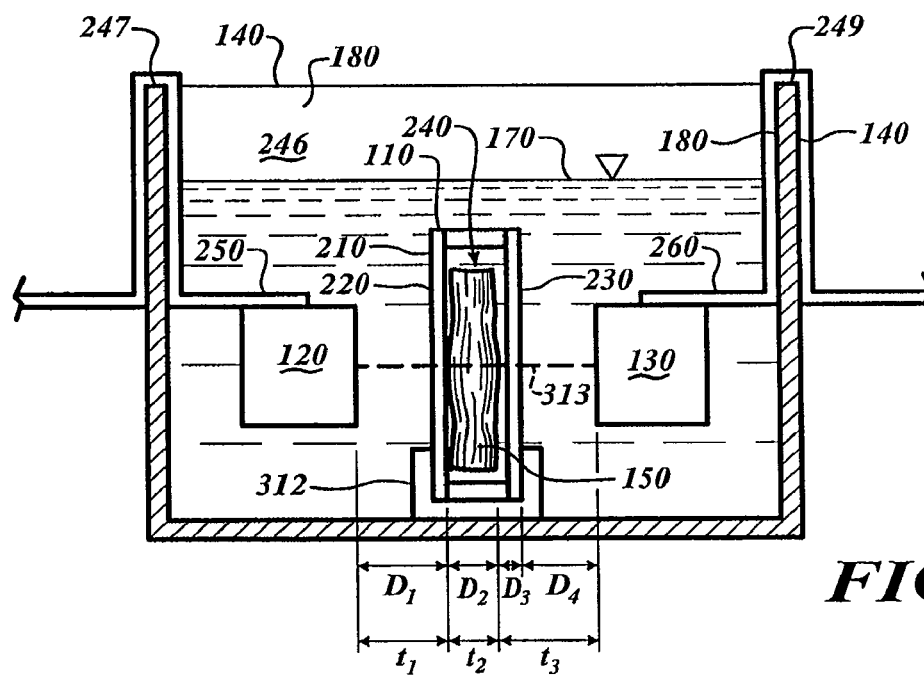
FIG. 2 is a side cross-sectional view of components of the processing system of FIG. 1.

FIG. 2 shows the container 140 with a chamber 180 filled with a processing media 170. The specimen holder 110, the transmitter 120, and the receiver 130 are submerged in the processing media 170. To fix a tissue specimen 150, the processing media 170 can be a fixative that diffuses through the specimen 150.

To analyze the specimen 150, the computing device 160 causes the transmitter 120 to output energy that passes through the specimen 150. The receiver 130 can receive the energy and can send signals to the computing device 160 in response to the received energy. The computing device 160 analyzes those signals to monitor processing. Once processing is complete, the specimen holder 110 can be conveniently removed from the container 140 or the processing media 170 can be deactivated.

The specimen 150 can be one or more biological samples. A biological sample can be a tissue sample (e.g., any collection of cells) removed from a subject. In some embodiments, a biological sample is mountable on a microscope slide and includes, without limitation, a section of tissue, an organ, a tumor section, a smear, a frozen section, a cytology prep, or cell lines. An incisional biopsy, a core biopsy, an excisional biopsy, a needle aspiration biopsy, a core needle biopsy, a stereotactic biopsy, an open biopsy, or a surgical biopsy can be used to obtain the sample. A freshly removed tissue sample can be placed in the processing media 170 within an appropriate amount of time to prevent or limit an appreciable amount of degradation of the sample 150. In some embodiments, the sample 150 is excised from a subject and placed in the media 170 within a relatively short amount of time (e.g., less than about 2 minutes, 5 minutes, 30 minutes, 1 hour, 2 hours, or the like). Of course, the tissue sample can be fixed as soon as possible after removal from the subject. The specimen 150 can also be frozen or otherwise processed before fixation.

To analyze the specimen 150 using acoustic energy, the transmitter 120 can output acoustic waves. The acoustic waves can be infrasound waves, audible sound waves, ultrasound waves, or combinations thereof. Propagation of the acoustic waves through the specimen 150 may change because of changes to the specimen 150. If the fixation process involves cross-linking, mechanical properties (e.g., an elastic modulus) of the specimen 150 may change significantly as cross-linking progresses through the tissue. The change in elastic modulus alters the acoustic characteristics of the specimen 150. Acoustic characteristics include, without limitation, sound speeds, transmission characteristics, reflectance characteristics, absorption characteristics, attenuation characteristics, or the like. To evaluate transmission characteristics, a time of flight (TOF) of sound (e.g., audible sound, ultrasound, or both), the speed of sound, or the like can be measured. The TOF is a length time that it takes for acoustic waves to travel a distance through an object or substance. In some embodiments, the TOF is the length of time it takes acoustic waves to travel through a specimen in comparison to the time to travel through the medium displaced by the specimen. In some embodiments, the time of flight of the medium and the measurement device (e.g., the holder) may be recorded prior to insertion of the sample and stored for later reference so that it can be used for temperature compensation, evaporative losses, compensation protocols, predictive modeling, or the like. The thickness of the specimen 150 can be sufficiently large to produce a measurable change in the TOF. In reflectance embodiments, the TOF can be the length of the time acoustic waves travel through a portion of the tissue specimen. For example, the TOF may be the length of time that the acoustic waves propagate within a portion of the tissue specimen. Thus, the TOF can be calculated based on acoustic waves that travel through the entire specimen, acoustic waves reflected by the tissue specimen, or both.

The speed of acoustic waves traveling through the specimen 150 is generally equal to the square root of a ratio of the elastic modulus (or stiffness) of the specimen 150 to the density of the specimen 150. The density of the specimen 150 may remain generally constant and, thus, changes in the speed of sound and the changes in TOF are primarily due to changes in the specimen's elastic modulus. If the density of the specimen 150 changes a significant amount, the sound speed changes and the TOF changes attributable to a change in elastic modulus can be determined by considering the specimen's changing density. Thus, both static and dynamic characteristics of the specimen 150 can be analyzed.

The processing system 100 can be a closed loop system or an open loop system. In closed loop embodiments, acoustic energy is transmitted through the specimen 150 based upon feedback signals from the receiver 130 and/or signals from one or more sensors configured to detect a parameter (e.g., temperature, pressure, or any other measurable parameter of interest) and to transmit (or send) signals indicative of the detected parameter. Based on those signals, the processing system 100 can control operation of the transmitter 120. Alternatively, the processing system 100 can be an open loop system wherein the transmitted acoustic energy is set by, for example, user input. It is contemplated that the processing system 100 can be switched between a closed loop mode and an open loop mode.

The specimen holder 110 can be portable for conveniently transporting it between various locations. In a laboratory setting, a user can manually transport it between workstations or between equipment. The illustrated specimen holder 110 is in the form of a cassette with a rigid main body 210 that surrounds and holds the specimen 150. The main body 210 includes a first plate 220 and a second plate 230 spaced apart from the first plate 220 to define a receiving space or chamber 240. The specimen 150 is positioned in the receiving space 240. The plates 220, 230 can have apertures or other features that facilitate transmission of acoustic energy. The shape, size, and dimensions of the specimen holder 110 can be selected based on the shape, size, and dimensions of the specimen 150. In various embodiments, the specimen holder can be (or include) a cassette, a rack, a basket, a tray, a case, foil, fabric, mesh, or any other portable holder capable of holding and transporting specimens. In some embodiments, the specimen holder 110 is a standard biopsy cassette that allows fluid exchange.

With continued reference to FIGS. 1 and 2, the transmitter 120 and the receiver 130 are fixedly coupled to walls 247, 249 of the container 140 by brackets 250, 260, respectively. The container 140 can be a tank, a tub, a reservoir, a canister, a vat, or other vessel for holding liquids and can include temperature control devices, a lid, a covering, fluidic components (e.g., valves, conduits, pumps, fluid agitators, etc.), or the like. To pressurize the processing media 170, the chamber 180 can be a pressurizable reaction chamber. Additionally the chamber 180 can be operated under a vacuum to reduce air bubble formation impeding sound transmission, and to support easier perfusion of fluids into the specimen holder 110 to displace trapped air.

To minimize, limit, or substantially eliminate signal noise, the container 140 can be made, in whole or in part, of one or more energy absorbing materials (e.g., sound absorbing materials, thermally insulating materials, or the like). The size and shape of the container 140 can be selected to prevent or substantially eliminate unwanted conditions, such as standing waves, echoing, or other conditions that cause signal noise. For example, if acoustic waves reflect off the inner surfaces of the container 140 and result in signal noise, the size of the container 140 can be increased.

The transmitter 120 can include a wide range of different types of acoustic elements that can convert electrical energy to acoustic energy when activated. For example, an acoustic element can be a single piezoelectric crystal that outputs a single waveform. Alternatively, an acoustic element may include two or more piezoelectric crystals that cooperate to output waves having different waveforms. The acoustic elements can generate acoustic waves in response to drive signals from the computing device 160 and can output at least one of audible sound waves, ultrasound waves, and infrasound waves with different types of waveforms. The acoustic waves can have sinusoidal waveforms, step waveforms, pulse waveforms, square waveforms, triangular waveforms, saw-tooth waveforms, arbitrary waveforms, chirp waveforms, non-sinusoidal waveforms, ramp waveforms, burst waveforms, pulse compression waveforms (e.g., window chirped pulse compression waveforms), or combinations thereof In some embodiments, the acoustic elements are transducers capable of outputting and detecting acoustic energy (e.g., reflected acoustic energy). Such embodiments are well suited to evaluate the specimen based on reflected acoustic waves. For example, the transmitter 120 can be in the form of an ultrasound transducer that transmits acoustic waves through at least a portion of the tissue sample 150. At least some of the acoustic waves can be reflected from the tissue sample 150 and received by the ultrasound transducer 120. A wide range of different signal processing techniques (including cross-correlation techniques, auto-correlation techniques, echoing analysis techniques, phase difference analysis, integration techniques, compensation schemes, synchronization techniques, etc.) can be used to determine a TOF of the acoustic waves. The computing device 160 can thus evaluate acoustic energy that is transmitted through the entire specimen 150 or acoustic energy reflected from the specimen 150, or both.

Audible sound waves may spread out in all directions, whereas ultrasound waves can be generally collimated and may reduce noise caused by reflectance and enhance transmission through the specimen 150. As used herein, the term "ultrasound" generally refers to, without limitation, sound with a frequency greater than about 20,000 Hz (hertz). For a given ultrasound source (e.g., an ultrasound emitter), the higher the frequency, the less the ultrasound signal may diverge. The frequency of the ultrasound signals can be increased to sufficiently collimate the signals for effective transmission through the processing media 170 and the specimen 150. To analyze a fragile specimen, relatively high frequency ultrasound can be used to minimize, limit, or substantially prevent damage to such specimen.

Additionally or alternatively, the transmitter 120 can include, without limitation, energy emitters configured to output ultrasound, radiofrequency (RF), light energy (e.g., visible light, UV light, or the like), infrared energy, radiation, mechanical energy (e.g., vibrations), thermal energy (e.g., heat), or the like. Light emitters can be light emitting diodes, lasers, or the like. Thermal energy emitters can be, without limitation, heaters (e.g., resistive heaters), cooling devices, or Peltier devices. Energy emitters can cooperate to simultaneously or concurrently deliver energy to the specimen 150 to monitor a wide range of properties (e.g., acoustic properties, thermal properties, and/or optical properties), to reduce processing times by keeping the media 170 at a desired temperature, enhance processing consistency, combinations thereof, or the like.

The receiver 130 can include, without limitation, one or more sensors configured to detect a parameter and to transmit one or more signals indicative of the detected parameter. The receiver 130 of FIGS. 1 and 2 includes at least one sensor configured to detect the acoustic energy from the transmitter 120. In other embodiments, the receiver 130 can include one or more RF sensors, optical sensors (e.g., visible light sensors, UV sensors, or the like), infrared sensors, radiation sensors, mechanical sensors (e.g., accelerometers), temperature sensors, or the like. In some embodiments, the receiver 130 includes a plurality of different types of sensors. For example, one sensor can detect acoustic energy and another sensor can detect RF energy.

The computing device 160 of FIG. 1 is communicatively coupled (e.g., electrically coupled, wirelessly coupled, capacitively coupled, inductively coupled, or the like) to the transmitter 120 and the receiver 130. The computing device 160 can include input devices (e.g., a touch pad, a touch screen, a keyboard, or the like), peripheral devices, memory, controllers, processors or processing units, combinations thereof, or the like. The computing device 160 of FIG. 1 is a computer, illustrated as a laptop computer.

Figure 3:
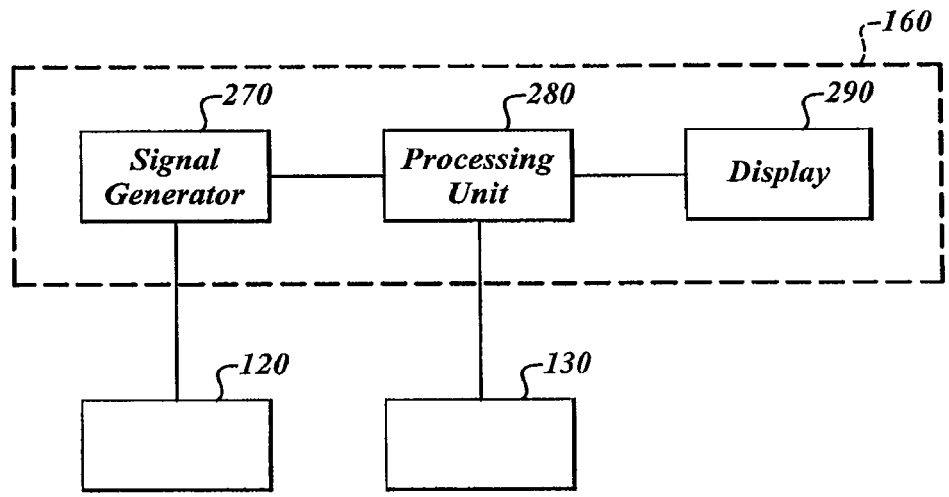
FIG. 3 is a block diagram of components of an analyzer and a computing device, in accordance with one embodiment.

FIG. 3 shows the computing device 160 (illustrated in dashed line) including a signal generator 270, a processing unit 280, and a display 290. The signal generator 270 can be programmed to output drive signals. Drive signals can have one or more sinusoidal waveforms, step waveforms, pulse waveforms, square waveforms, triangular waveforms, saw-tooth waveforms, arbitrary waveforms, chirp waveforms, non-sinusoidal waveforms, ramp waveforms, burst waveforms, or combinations thereof. The waveform can be selected based on, for example, user input, stored parameters, or input from another system (e.g., a tissue preparation unit, staining unit, etc.). By way of example, the signal generator 270 can include an arbitrary function generator capable of outputting a plurality of different waveforms. In some embodiments, the signal generator 270 is an arbitrary signal generator from B&K Precision Corp. or other arbitrary signal generator.

The computing device 160 is communicatively coupled to a tissue processing unit that applies any number of substances to prepare the specimen for embedding. The computing device 160 can prepare a tissue preparation protocol that is used by the tissue processing unit. The tissue preparation protocol can include a length of processing time for a particular substance, target composition of a substance, temperature of a particular substance, combinations thereof, or the like.

The processing unit 280 can evaluate the change in the TOF of sound in the specimen 150 by, for example, comparing the acoustic waves outputted by the transmitter 120 to the acoustic waves detected by the receiver 130. This comparison can be repeated any number of times to monitor the fixation state of the specimen 150. In some embodiments, the processing unit 280 determines a first length of time it takes the acoustic waves to travel through the specimen 150. The processing unit 280 then determines a second length of time it takes a subsequently emitted acoustic wave to travel through the specimen 150. The first length of time is compared to the second length of time to determine, without limitation, a change in speed (e.g., acceleration) of the sound waves, an absolute and/or relative change in TOF, change in distance between the transmitter 120 and the receiver 130, change in temperature and/or density of the processing media 170, or combinations thereof. The processing unit 280 can use different types of analyses, including a phase shift analysis, an acoustic wave comparison analysis, or other types of numerical analyses.

To store information, the computing device 160 can also include memory. Memory can include, without limitation, volatile memory, non-volatile memory, read-only memory (ROM), random access memory (RAM), and the like. The information includes, but is not limited to, protocols, data (including databases, libraries, tables, algorithms, records, audit trails, reports, etc.), settings, or the like. Protocols include, but are not limited to, baking protocols, fixation protocols, tissue preparation protocols, staining protocols, conditioning protocols, deparaffinization protocols, dehydration protocols, calibration protocols, frequency adjustment protocols, decalcification protocols, or other types of routines. Protocols that alter or impact tissue density or sound transmission can be used to control the components of the computing device 160, components of the analyzer 114, microscope slide processing units, stainers, ovens/dryers, or the like. Data can be collected or generated by analyzing the specimen holder 110, the processing media 170, the specimen 150, or it can be inputted by the user.

The computing device 160 can evaluate different acoustic properties. Evaluation of acoustic properties can involve comparing sound speed characteristics of the specimen, comparing sound acceleration in the specimen, analyzing stored fixation information, and analyzing TOF. Analysis of the TOF may involve, without limitation, evaluating the total TOF, evaluating changes in TOF over a length of time (as discussed above), evaluating rates of change in TOF, generating TOF profiles, or the like. The stored fixation information can include, without limitation, information about sound speeds for different types of tissue, fixation rates, predicted fixation time, compensation protocols, percent cross-linking, TOF profiles, tissue compositions, tissue dimensions, algorithms, waveforms, frequencies, combinations thereof, or the like. In some embodiments, the computing device 160 evaluates at least one of the TOF, a TOF change, amplitude of the sound waves, an intensity of the sound waves, phase shifts, echoing, a temperature and/or density of the specimen 150, and a temperature and/or density of the processing media 170.

The computing device 160 can select, create, or modify fixation settings, with or without prior knowledge of specimen history, specimen fixation state, or type of tissue so as to improve the reliability and accuracy of diagnosis, especially an advanced diagnosis. Fixation settings include, without limitation, length of fixation time (e.g., minimum fixation time, maximum fixation time, ranges of fixation times), composition of the processing media, and temperature of the processing media. By way of example, if the specimen 150 has a known fixation state, an appropriate fixation protocol can be selected based, at least in part, on the known fixation state. If the specimen 150 has an unknown fixation state, the analyzer 114 is used to obtain information about the fixation state. For example, the analyzer 114 can obtain information about a specimen that is already partially or completely fixed. Protocol settings can be selected based, at least in part, on the obtained information. The protocol settings can include tissue preparation settings, fixation protocol settings, reagent protocol settings, or the like. In some embodiments, reagent protocol settings (e.g., types of IHC/ISH stains, staining times, etc.) can then be selected to match/compensate for the fixation state based, at least in part, on information from the analyzer 114. The analyzer 114 can thus analyze unfixed, partially fixed, or completely fixed specimens.

To process multiple tissue specimens, the processing system 100 can dynamically update fixation settings. Fixation settings can be generated by analyzing the illustrated specimen 150. Another specimen taken from the same biological tissue as the specimen 150 can be processed using the new fixation settings. In this manner, the fixation process can be dynamically updated.

Figure 4:
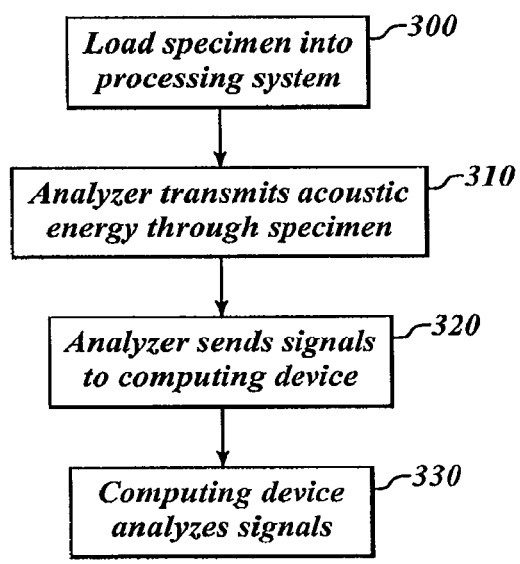
FIG. 4 is a flow diagram of an exemplary method of processing a specimen, in accordance with one embodiment.

FIG. 4 shows an exemplary method of fixing the specimen 150 to protect the specimen 150 from, for example, putrefaction, autolysis, or the like. In general, the specimen 150 can be loaded into the processing system 100. The processing media 170 contacts and begins to fix the specimen 150. The analyzer 114 monitors the fixation process. After the specimen 150 is sufficiently fixed, the specimen 150 is taken out of the fixation media 170 to conveniently avoid under-fixation and over-fixation. Details of this fixation process are discussed below.

At step 300 of FIG. 4, the specimen 150 is loaded into the specimen holder 110. To open the specimen holder 110, the plates 220, 230 can be separated. The plates 220, 230 can be coupled together to loosely hold the specimen 150. In some embodiments, the specimen holder can be a standard Cellsafe™ tissue cassette for biopsy samples from Cellpath Ltd or other types compatible with acoustic transmission. The closed specimen holder 110 is manually or automatically lowered into the container 140 and held in a docking station 312 (see FIGS. 1 and 2). The docking station 312 can be a clamp, a gripping mechanism, or other component suitable for retaining the specimen holder 110.

The processing media 170 begins to diffuse through the specimen 150 to begin the fixation process. The fixation processes may involve limiting or arresting putrefaction, limiting or arresting autolysis, stabilizing proteins, and otherwise protecting or preserving tissue characteristics, cell structure, tissue morphology, or the like. The fixative can include, without limitation, aldehydes, oxidizing agents, picrates, alcohols, or mercurials, or other substance capable of preserving biological tissues or cells. In some embodiments, the fixative is neutral buffered formalin (NBF). In some fixation processes, the media 170 is a fixative that causes cross-linking of the specimen 150. Some fixatives may not cause cross-linking.

At 310, the analyzer 114 transmits acoustic energy through the specimen 150. The signal generator 270 (see FIG. 3) can output a drive signal to the transmitter 120 which, in turn, emits acoustic energy that is ultimately transmitted through the specimen 150.

At 320, the receiver 130 detects the acoustic energy and outputs receiver signals to the computing device 160 based on the detected acoustic energy. The receiver signals may or may not be processed (e.g., amplified, modulated, or the like).

At 330, the computing device 160 analyzes the receiver signals. The computing device 160 can control the processing system 100 to enhance processing reliability, reduce processing times, improve processing quality, or the like. For example, the temperature of the processing media 170 of FIG. 2 can be controlled to enhance diffusion of the media 170 to reduce processing times.

Once the tissue specimen 150 reaches a desired fixation state, the specimen holder 110 is removed (e.g., manually or automatically) from the media bath. The fixed specimen 150 can be embedded, sectioned, and stained without performing tests that cause specimen waste.

The processing system 100 of FIGS. 1 and 2 can include any number of thermal devices, mechanical devices, sensors, or pumps. The thermal devices can regulate the temperature of the media 170 and can include one or more heaters, cooling devices, Peltier devices, or the like. The mechanical devices can include, without limitation, agitators (e.g., fluid agitators), mixing devices, vibrators, or the like. The sensors can be, without limitation, acoustic sensors, motion sensors, chemical sensors, temperature sensors, viscosity sensors, optical sensors, flow sensors, position sensors, pressure sensors, or other types of sensors. The sensors can be positioned at various locations about the chamber 180.

TOF measurements can be used to monitor fixation processes. Theoretical changes in TOF can be calculated based on the distances between components in the processing system 100, the dimensions of the specimen 150, a length of a sound path 313 (see FIG. 2) along which the acoustic energy travels, and the acoustic properties of the fixative media 170 and specimen holder 110. The computing device 160 can analyze calculated values to determine fixation settings, such as initial fixation settings.

Table 1 below shows calculated theoretical changes in TOF based on the speed of sound in water (1,482 m/s), the speed of sound in unfixed muscular tissue (1,580 m/s), and the speed of sound in fixed muscular tissue (1,600 m/s). The theoretical calculations can be compared to measured values in order to modify the fixation process. In some embodiments, the theoretical calculations are used to determine initial settings for the fixation process. The initial settings may include waveforms, amplitude of acoustic energy, frequency of acoustic energy, processing temperatures, or the like.

TABLE 1

| Sound path | Dimension | Distance [mm] | TOF [us] | TOF after fixation [us] |
|---|---|---|---|---|
| transmitter -> cassette/specimen | D1 | 20 | 29.6 | |
| specimen | D2 | 4 | 6.32 | 6.4 |
| specimen -> specimen holder | D3 | 1 | 1.48 | |
| Specimen holder -> receiver | D4 | 25 | 37 | |
| TOTALS | | 50 | 74.4 | 74.48 |
| | | | delta [ns] | 80 |

FIG. 2 shows the distance $D_1$ from the transmitter 120 to the specimen 150, the distance $D_2$ between opposing surfaces of the specimen 150, the distance $D_3$ from the specimen 150 to the outer surface of the second plate 230, and the distance $D_4$ from the specimen holder 110 to the receiver 130. The sound speeds and densities of common tissue types are well known in the art. These known values can be used to calculate the change in TOF and determine initial fixation settings. Because sound speeds are dependent on the temperature of the medium and the distance of the measurement channel may be dependent on thermal expansion coefficients of the related components, a reference TOF measurement of the medium and the measurement channel at a given temperature of the medium and the test environment may be performed in some embodiments. This reference measurement may be used to compensate for the TOF measurements of the specimen.

The total TOF can be determined by the individual travel times of the sound waves traveling first through a portion of the media 170 for the time "t1" across the distance $D_1$, followed by the time "t2" as the sound waves travel across the distance $D_2$, and finally the time "t3" as the sound waves travel the remaining distances $D_3$ and $D_4$. Thus, the total TOF=t1+t2+t3. Changes in the total TOF can be measured and related to the state of fixation and thus relate primarily or only to the time "t2." The information of an unimpeded sound path (e.g., a sound path without a sample insertion as a reference) may be used to identify variation of the total TOF due to, for example, changes of the media 170 (e.g., temperature changes, density changes, etc.).

Figure 5:
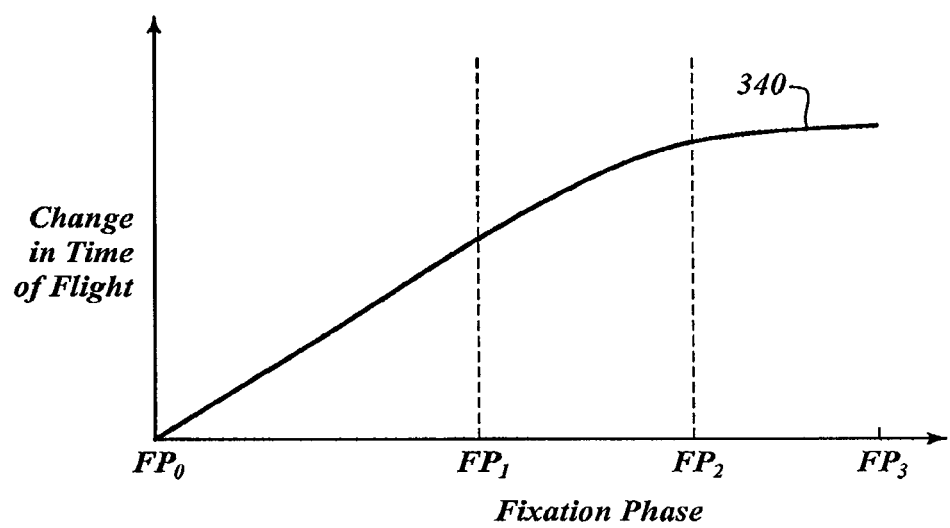
FIG. 5 is a graph of fixation phase versus change in time of flight.

Different types of tissue can have different acoustic characteristics. FIG. 5 is a non-limiting exemplary graph of fixation phase versus change in a TOF. A curve 340 can be generated by analyzing a specimen. Different types of tissue may generate different types of curves, as discussed below in connection with FIGS. 30-38. The computing device 160 can correlate the different curves to different tissue types. To process a fresh specimen, a curve can be selected corresponding to the same or similar tissue type as the fresh specimen. The computing device 160 can provide an appropriate processing protocol based on the curve. The protocol can include, without limitation, a fixating protocol, a tissue preparation protocol, an embedding protocol, a decalcification protocol, a staining protocol, or combinations thereof. Information can also be obtained while the protocol is performed to modify the protocol or select another protocol. By way of example, the curve 340 can be used to determine, at least in part, when to remove a specimen from a fixation media.

Curve fitting techniques using polynomials, trigonometric functions, logarithmic functions, exponential functions, interpolations (e.g., spline interpolations) and combinations thereof can be used to generate the curve 340 which approximates collected data. Some non-limiting exemplary curve fitting techniques are discussed in connection with FIGS. 13-16.

At an initial fixation phase $FP_0$ in FIG. 5, the unfixed specimen 150 is exposed to the processing media 170. The outermost portions of the specimen 150 begin to f As the fixation phase increases from $F1_0$ to $FP_1$, the change in TOF gradually increases with respect to the fixation phase. From $FP_1$ to $FP_2$, the cross-linking approaches the interior regions of the specimen 150. The change in TOF is nonlinear with respect to the fixation phase. As the fixation phase approaches $FP_2$, the rate of change of the TOF change begins to rapidly decrease. From $FP_2$ to $FP_3$, the specimen 150 becomes saturated until there may be over-saturation at about $FP_3$. Approaching $FP_3$, the slope of the curve 340 continues to decrease as it approaches zero, corresponding to when the specimen 150 may be at risk of over-fixation. The fixation process can be controlled based on, for example, the slope of the curve 340, a minimum TOF change, a maximum TOF change, combinations thereof, or the like.

A fixation predictive algorithm can be used to determine a desired processing time to achieve a desired level of fixation. The computing system 160 can store and select fixation predictive algorithms based on the desired amount of cross-linking. If the fixation media 170 causes cross-linking at a non-linear rate, a non-linear fixation predictive algorithm can be selected. For example, cross-linking could exhibit exponential decay so an exponential decay curve can be used to estimate an end of processing time. The desired level of cross-linking can be selected based on the tissue type, the analysis to be performed, the expected storage time, or other criteria known in the art. For example, the predictive curve can be used to determine a predicted stopping time for which cross-linking should be about 99% complete.

A Levenberg-Marquardt algorithm or other type of non-linear algorithm can be used to generate an appropriate best fit curve. In some predictive protocols, the Levenberg-Marquardt algorithm uses an initial value to generate a curve. A damping-undamping scheme can produce the next iteration. Non-limiting exemplary damping-undamping schemes are described in the paper "Damping-Undamping Strategies for the Levenberg-Marquardt Nonlinear Least-Squares Method" by Michael Lampton. The closer to the actual curve of the initial value, the more likely it is that the algorithm will provide the desired best-fit curve. In some protocols, a plurality of values in the data set (e.g., a first value, a middle value, and a last value) are used to produce an exponential curve that fits the three values. The initial values can be selected based on known values for similar tissue specimens. After performing the iterative process, a best fit curve is generated. The best-fit curve can be used to determine the predicted state of the specimen at different times during processing. This can be helpful to develop a schedule to increase processing throughput, especially if the processing system allows for individual processing, as discussed in connection with FIG. 21.

Figure 6:
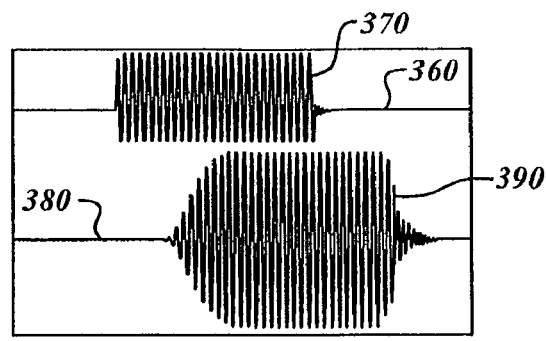
FIG. 6 is a plot showing a timing relationship between an outputted signal and a received signal.

FIG. 6 shows a timing relationship between a signal 360 from the transmitter 120 and a detected signal 380. The signal 360 can have a sufficient number of signal bursts to evaluate phase changes of waves entering and exiting the specimen 150 at a particular distance. By way of example, acoustic waves 370 of the signal 360 are illustrated as a pulse burst and can be a 1 MHz sine burst with 53 cycles, 5.3 ms repetition rate, and a 7.4 V amplitude. Other acoustic waves with different pulse bursts, numbers of cycles, repetition rates, amplitudes, etc. can also be used. The detected signal 380 corresponds to the signal received by the receiver 130. A pulse burst 390 corresponds to the signal burst 370.

Figure 7:
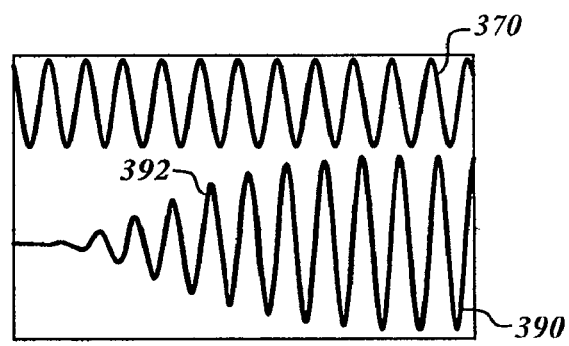
FIG. 7 is an enlarged view of a portion of the outputted signal and a portion of the received signal.
Figure 8:
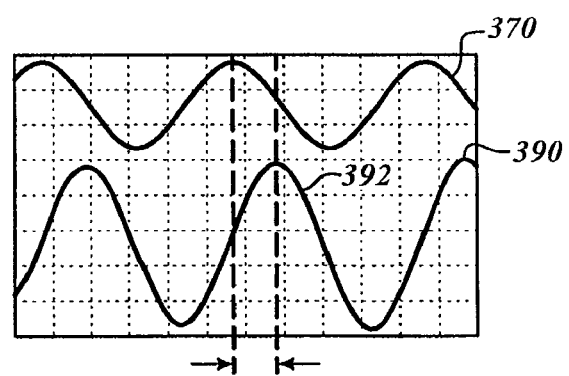
FIG. 8 is a detailed view of a portion of the outputted signal and a corresponding portion of the received signal.

FIGS. 7 and 8 show the relationship between the signal burst 370 and the received acoustic waves 390. A change in TOF, if any, can be determined based on a comparison of the waves 370, 390. If the TOF does not change, there will be no phase shift between the waves 370, 390 over time. If there is a TOF change, there will be a phase shift over time. For example, at the fifth wave 392, there is about 38.28 µs phase delay or shift, measured against the reference signal 370. As a sample undergoes fixation, the sound speed in most types of tissue (e.g., muscle tissues, connective tissues, etc.) typically increases. However, some fatty tissues will cause a decrease of sound speed during fixation. The system 100 can detect a relative phase angle difference resulting from a phase shift caused by an early or late arrival of the pulse packet 390.

Figure 9:
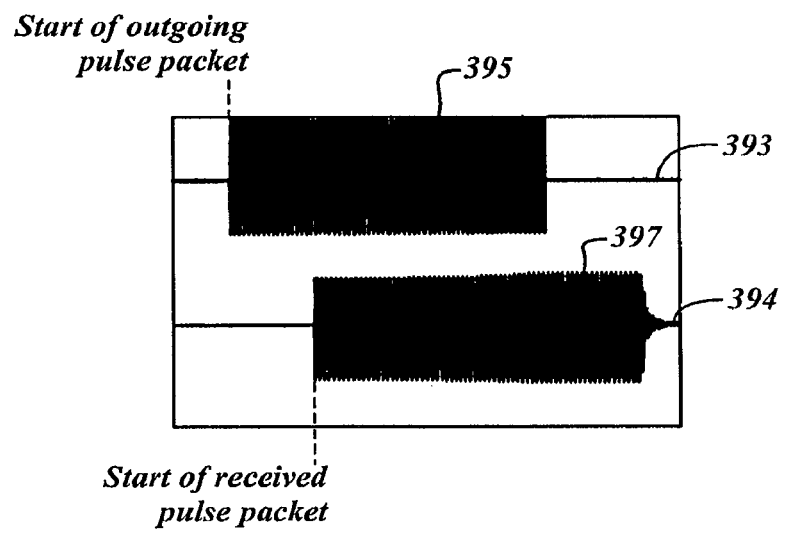
FIG. 9 is a plot showing a timing relationship between an outputted signal, a received signal, and a comparison curve.
Figure 9:
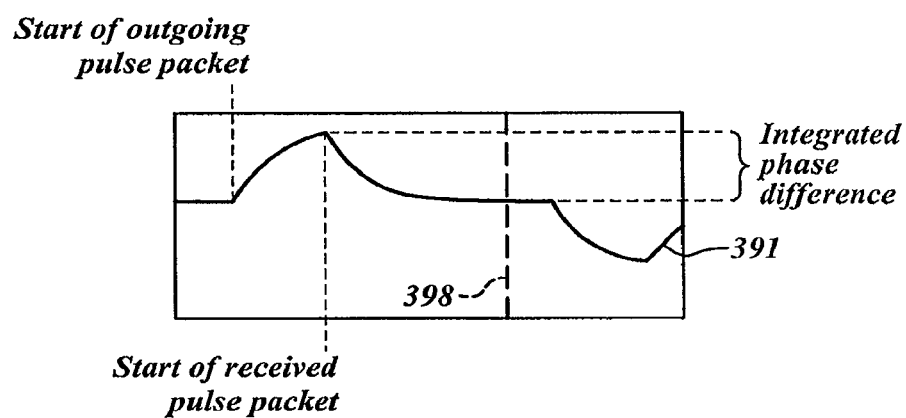

FIG. 9 shows the relationship of outputted waves 393, received waves 394, and a comparison curve 391. The comparison curve 391 shows phase differences, illustrated as an analog voltage output, that reflect an integrated phase difference accumulated from a comparison (e.g., a synchronous comparison) of two wave packets 395, 397. The integrated phase difference can be used to determine when to evaluate a phase difference between the two waves 393, 394 or what part of the waves 393, 394 to compare.

A trigger point, indicated by a dashed line 398, can be communicated to the computing device (e.g., a data capture system). The trigger point 398 can be selected based on a settling point, rate of change, or the like of the curve 394. An electronic data capture system of the system 160 can analyze the waves 393, 394 at the trigger point and can have a resolution around 1 ns or better (based on +/−1 sd at n=7 captured pulse packets) in shadowed transmission mode. Any number of trigger points can be selected along the curve 391 based on the desired amount of sampling.

Figure 10A:
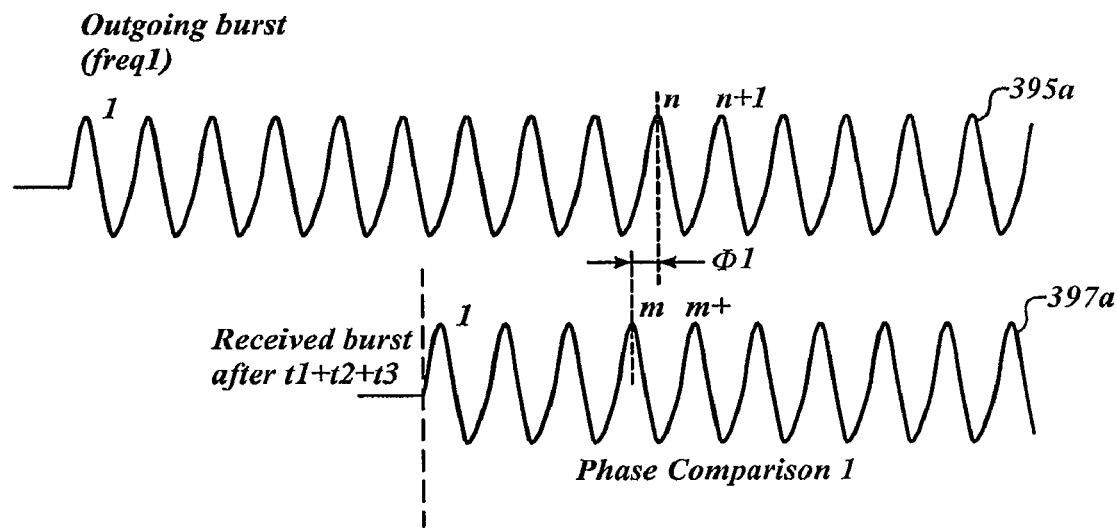
FIG. 10A is a plot showing a timing relationship between an outputted signal and a received signal, in accordance with one embodiment.
Figure 10B:
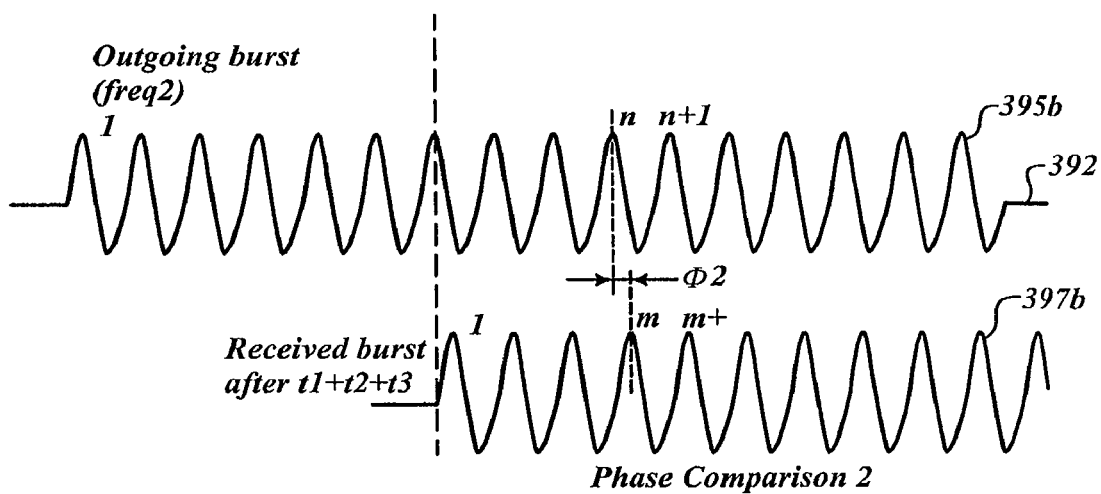
FIG. 10B is a plot showing a timing relationship between an outputted signal and a received signal, in accordance with yet another embodiment.

FIGS. 10A and 10B show phase angle relationships based on the frequency of outgoing waves. In FIG. 10A, an outgoing burst signal 395a, a received burst signal 397a, and an initial phase relationship Ø1 caused by the signal 397a traveling through the sample 150. FIG. 10B shows an outgoing burst wave 395b outputted at a frequency 2 higher than the frequency 1 of wave 395a of FIG. 10A. The outgoing wave 395b of FIG. 10B has a reduced wavelength as compared to the outputted wave 395a. As such, the phase relationship Ø1 is different from the phase relationship Ø2. Because the TOF is primarily or only dependent on the distance of travel and the density of the media or sample, the phase relationship can be freely configured by selecting the frequency (or other characteristics) of the outgoing waves. Accordingly, the computing system 160 an select the frequency of the outgoing wave based on a desired phase relationship.

Frequencies and the resulting phase relationships can be correlated to determine how changes of the outgoing frequency will result in phase relationship changes, which in turn can be used to monitor the sample 150. A monitoring protocol can include, without limitation, outputting a plurality of waves with different frequencies to generate a plurality of phase relationships. A comparison (e.g., an extended phase range comparison) can be accomplished by adaptively monitoring phase angle progression. Outgoing frequencies can be changed (e.g., incrementally changed) by the signal generator 270 to keep the phase relationship in the favorable range. The phase angle change is linearly dependent on the frequency change and therefore can be added successively as an absolute TOF increment to any additional changes observed by the phase comparison itself. Because most reactions being monitored are in a time range of several tens of minutes, an adaptive frequency change can be easily achieved.

Figure 11:
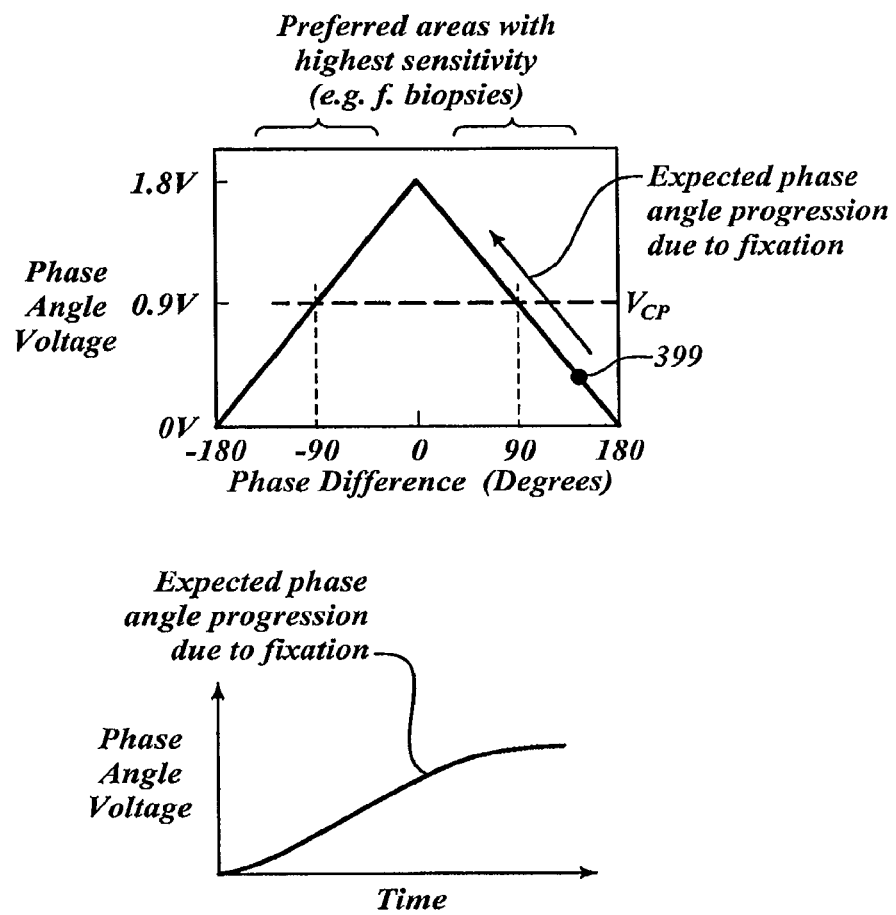
FIG. 11 is a graph of phase difference versus phase angle voltage and a plot showing time versus phase angle voltage with an expected phase equal progression due to fixation.

The base wavelength for an ultrasound transducer may result in a phase detection limit. For example, the ultrasound transducer 120 may output a signal at a frequency of about 4 MHz, 0-180 degrees, at about the 125 ns range. Different ultrasound receivers may provide a larger phase angle range, but depth resolution for the target thickness may be limited to thicker samples. For greater phase angle differences (e.g., greater than 180 degrees), the integrated voltage can be reversed in polarity, or repeat itself for phase angle differences greater than 360 degrees. Because monitoring of fixation may rely on relative phase angle changes, the initial phase angle can be optimized on a target, such as by varying the base wavelength in the arbitrary function generator 170 to establish an initial setting with a favorable phase relationship, for example, the point 399 in the graph of FIG. 11. FIG. 11 also shows phase differences that provide high sensitivity. Other methods may not rely on phase comparison measurements and instead utilize chirped pulse excitation and correlation or convolution methods to calculate absolute TOF with similar precision and resolution.

A wide range of compensation techniques can be utilized to analyze TOF measurements. One compensation technique for relatively large phase shifts during TOF monitoring relies on reduction principles. A mathematical reduction principle can use, for example, multiple discrete excitation frequencies (=wavelength scans) sent in succession of bursts at the same target location. A change in time, ΔT, can represent the actual time delay between when a wave is sent and when the wave is received. A plurality of waves of different wavelengths, $\lambda_1, \lambda_2, \ldots, \lambda_n$, can be emitted. The received waves can be compared with the outgoing waves to determine corresponding phase changes, $\Delta\theta_{\lambda_1}, \Delta\theta_2 \ldots, \Delta\theta_{\lambda_n}$. The computing device 160 can narrow down the actual value of $\Delta T$ to a subset of values which is much smaller than the set of all possible values for $\Delta T$. If there is a range of wavelength scans, $\lambda_1, \lambda_2, \ldots, \lambda_n$, and their corresponding phase changes, $\Delta\theta_{\lambda_1}, \Delta\theta_{\lambda_2}, \ldots \Delta\theta_{\lambda_n}$, the computing device 160 can use each reading to further narrow down an estimated $\Delta T$ until there is only one feasible value $\Delta T$.

The change in phase $\Delta\theta_\lambda$ can be measured at a given frequency, $\lambda$. Because there may be many values for $\Delta T$ that would yield the same $A\Delta\theta_\lambda$, the $\Delta T$ can be estimated or predicted based, at least in part, on a specific $\Delta\theta_\lambda$ since most values for $\Delta T$ would not yield a given $\Delta\theta_\lambda$ (the true value of $\Delta T$ satisfies the equation $\Delta T = N/(2\lambda) + \Delta\theta_\lambda$ for some integer N). A program can be used to at least narrow down the true value of $\Delta T$ to a subset of values which is much smaller than the set of all possible values for $\Delta T$ based on an estimated $\Delta T$ from a specific $\Delta\theta_\lambda$. The computing device 160 can generate a range of wavelength scans, $\lambda_1, \lambda_2, \ldots, \lambda_n$, and their corresponding phase changes, $\Delta\theta_{\lambda_1}, \Delta\theta_{\lambda_2}, \ldots, \Delta\theta_{\lambda_n}$, as detailed above.

An interactive algorithm can be used to determine AT and can be used to minimize or avoid problems associated with solving for $\Delta T$ algebraically (e.g., problems attributable to the noisy nature of TOF measurements). In some interactive algorithms, a $\Delta T$ is estimated or predicted. A theoretical $\Delta\theta_\lambda$ can be determined for that $\Delta T$ and can be compared to measured $\Delta\theta_\lambda$'s to assign a penalty function. The penalty function can be the sum of the squared differences between the theoretical $\Delta\theta_\lambda$'s and the measured $\Delta\theta_\lambda$'s. The true value of $\Delta T$ can be the minimizer of the penalty function. The method for minimizing this function can be determined using different techniques, such as a sweep of values or a binary search. Additionally or alternatively, a gradient descent, Newton method (including Gauss—Newton algorithm), or Levenberg-Marquardt method could be used. Other algorithms can also be utilized, if needed or desired. In some protocols, one or more out-of-range values (e.g., values <0.2 and/or values >1.5) can be discarded. The out-of-range values can be selected based on criteria corresponding to characteristics of the tissue specimen.

A phase detection algorithm can be used to compare an outgoing wave with a corresponding received wave. One type of phase detection algorithm is a range extension algorithm involving multiple wavelengths of phase angle changes for acoustic speed measurements. When the speed of acoustic waves changes significantly, the computing device 160 may base wave comparisons on a different period of the wave than it started on, resulting in a sudden change from an increasing TOF to a decreasing TOF or resulting in a sudden change from a decreasing TOF to an increasing TOF. The sudden change is attributable to the comparison of different phases, thereby leading to artificial data. Rate of changes in TOF can be evaluated to determine whether the TOF changes are artificial changes due to such out of phase comparisons. For example, the second derivative of the TOF curve can be used to determine whether a local maximum TOF or a local minimum in TOF is a natural change in TOF or an artificial change in TOF.

Figure 12:
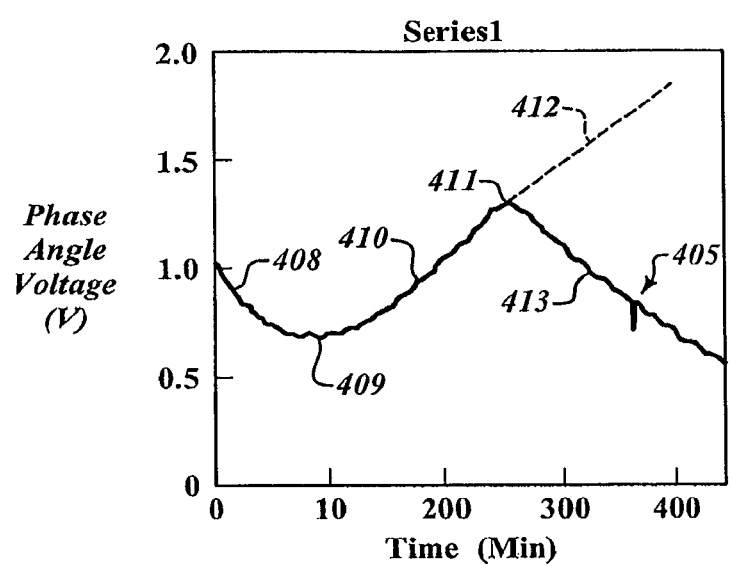
FIG. 12 is a plot of fixation time versus phase angle voltage.

FIG. 12 shows a graph of time versus TOF signal. A curve 405 gradually decreases at 408 to a local minimum 409. The curve 405 then increases at 410 to an artificial local maximum 411. The actual TOF continues to gradually increase, as indicated by the dashed curve 412. The peak 411 is generated based on an out of phase comparison. The curve 405 at 413 continues to decrease at time greater than 260 based on the out of phase comparison. As shown in FIG. 12, there is a significant difference between the actual TOF 412 and the artificial TOF 413.

Figure 13:
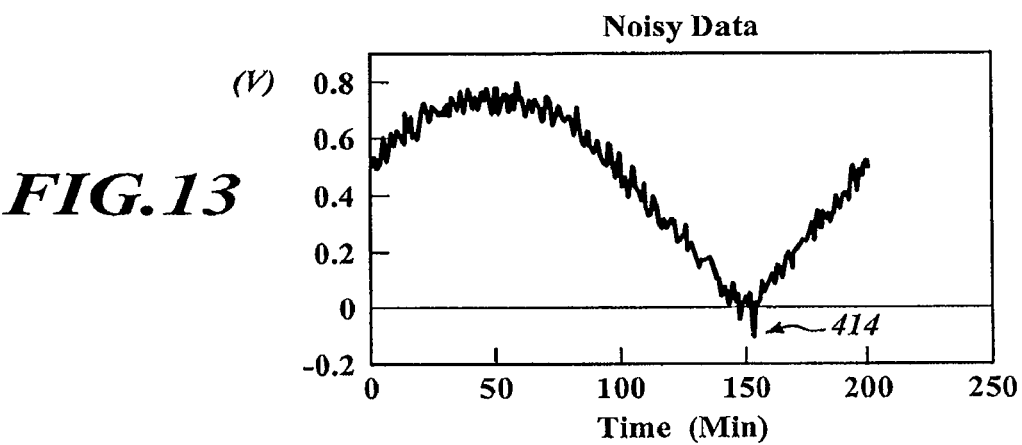
FIG. 13 is a plot of fixation time versus phase angle voltage.

Artificial measurements can be identified to avoid the peak 411. By way of example, FIG. 13 is a graph of time versus TOF with noisy data. The TOF increases from a time=0 minutes to about t=55 minutes. The TOF gradually decreases from 55 minutes to about 150 minutes. The TOF suddenly begins to increase at about 150 minutes. A program can determine whether the sudden change in TOF is accurate or artificial.

Figure 14:
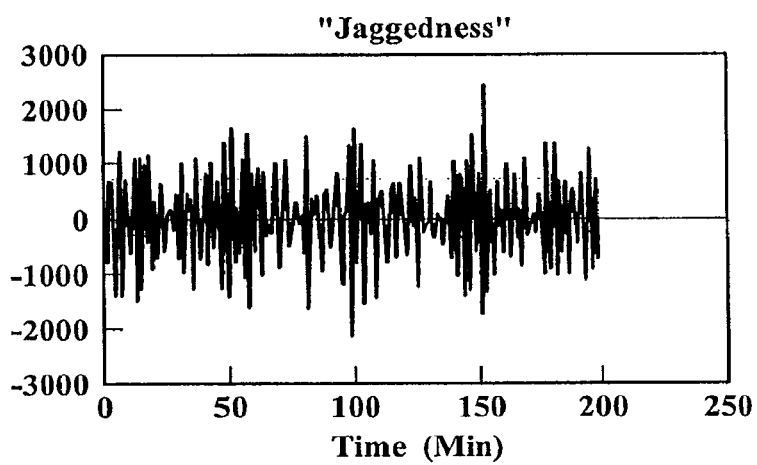
FIG. 14 is a plot showing jaggedness of the data of FIG. 13.

FIG. 14 shows a plot generated using numerical differentiation (e.g., finite-difference methods) of the data of FIG. 13 which increase the signal-to-noise ratio resulting in jaggedness curve 414 that is not suitable for determining whether changes in TOF are natural or artificial. The spike at time of about 155 corresponds to artificial changes from a decreasing TOF to an increasing TOF based on a comparison between difference phases of waves. Based on the numerous large spikes in FIG. 14, it may be difficult to accurately determine whether a spike corresponds to an artificial or a natural change in TOF.

Figure 15:
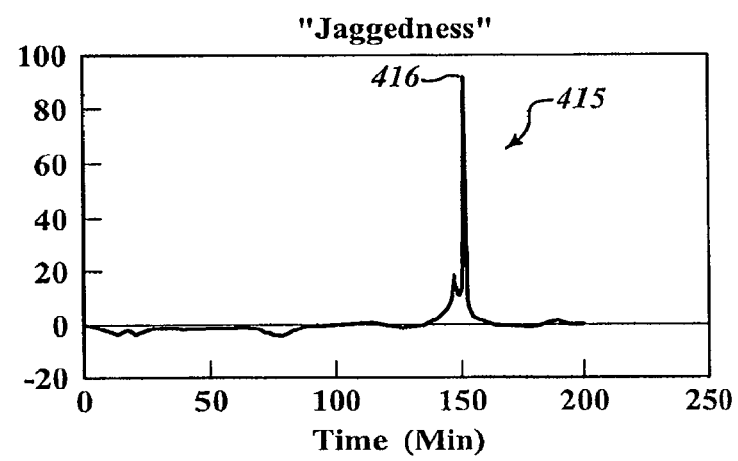
FIG. 15 is a plot of jaggedness generated using a smoothing algorithm and the data of FIG. 13.

FIG. 15 shows jaggedness of the noisy two-peak curve of FIG. 13 using a smoothing algorithm, such as a total variation smoother algorithm. The total variation smoothing algorithm can be used to smooth the raw data of FIG. 13 before generating the jaggedness plot. A compensation program can recognize that the change in time of flight at about t=150 is artificial and recompare different phases of the waves to ensure that the general trend of the time of flight as t approaches 150 is generally maintained. The large spike 416 at 150 minutes can be conveniently identified in FIG. 15, while the natural peak is barely identifiable. A compensation program can be used to compensate for the spike 416. Such compensation programs can include, without limitation, an algebraic algorithm or other type of compensation algorithm.

Figure 16:
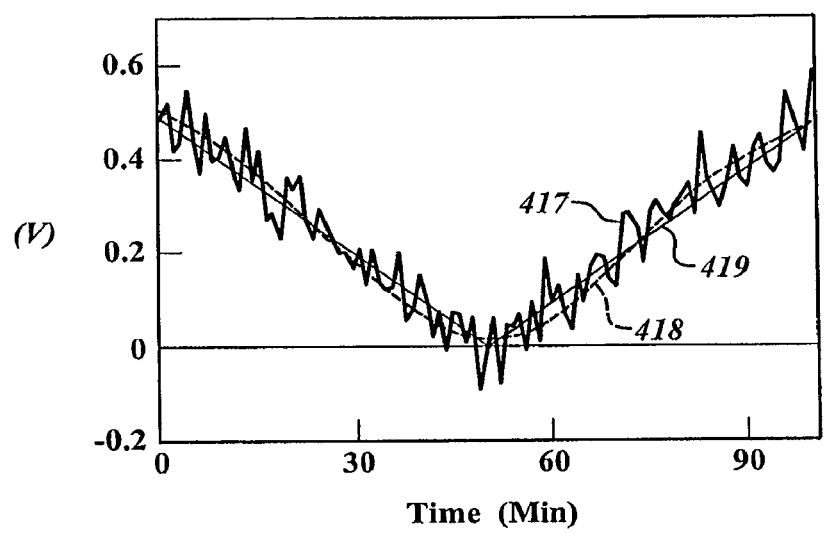
FIG. 16 is a plot of curves generated using different algorithms for analyzing noisy data.

Noise can be reduced without eliminating desired data. One noise-reducing method that does not over-smooth data (e.g., cusps) is discussed in "Numerical Differentiation of Noisy, Nonsmooth Data" by Rick Chartrand, published by Los Alamos National Laboratory, Dec. 13, 2005. The method is an example of a total variation smoother which smoothes noise while preserving true cusps, thereby minimizing, eliminating, or limiting only unwanted noise. FIG. 16 shows a data plot 417, a first smoothed curve 418 (shown in dashed line), and a second smoothed curve 419. Numerous cusps of the data plot 417 are eliminated in the first smoothed curve 418 which was generated using a numerical differentiation algorithm designed to remove sharp peaks/valleys. The second curve 419 was generated using total variation smoother algorithm which preserves true cusps. Thus, the second curve 419 is well suited for identifying inaccurate (e.g., artificial peaks/valleys) TOF signals at the time of 49 minutes as compared to the first smoothed curve 418.

Movement of tissue within a specimen holder can lead to inaccurate measurements. If the tissue specimen 150 moves inside the specimen holder 110, the change in position of the specimen can significantly alter measurements for monitoring cross-linking, changes in specimen density, or the like. Averaging, comparing, or otherwise analyzing data obtained from one or more analyzers, as discussed in connection with FIG. 18, can be used to compensate for such movement. The computing device 160, for example, can include different types of algorithms that use data obtained for a plurality of analyzers. If tissue shifts within the specimen holder (e.g., when a cassette is jarred or a cassette moves rapidly through media), movement of the tissue relative to the cassette can be accounted for to avoid changes attributable to tissue migration.

Tissue analyzers described herein can also analyze tissue specimens after fixation. For example, the tissue analyzer 114 of FIGS. 1 and 2, or a modified tissue analyzer, can obtain information about a tissue sample embedded in a material, a cut mountable section (e.g., a cut strip of embedded tissue), or the like. Information about the specimen can thus be obtained before fixation/processing, during fixation/processing, and after fixation/processing. Specimens can be analyzed any number of times throughout processing to ensure that the specimen is properly prepared for examination. One method of analyzing fixed tissue is described below with respect to an embedded specimen.

In some embodiments, the specimen 150 is a block of embedding material containing a tissue sample. The embedding material can have mechanical properties that may facilitate sectioning. Materials for embedding include, but are not limited to, paraffin, resin (e.g., plastic resins), polymers, agarose, nitrocellulose, gelatin, mixtures thereof, or the like. Paraffin is a white or generally colorless water insoluble solid substance that is resistant to many reagents. Paraffin can be a mixture of hydrocarbons chiefly of the alkaline series obtained from petroleum. A wide range of different mixtures of similar hydrocarbons can be used to make paraffin, and these mixtures can be solid, semi-solid, and/or oily. The acoustic properties of these types of embedding materials may be known or may be determined using the analyzer 114. The speed of sound traveling through the block (including the tissue) can be analyzed to select an appropriate protocol to be performed on the tissue sample. A wide range of different variables (e.g., dimensions of the block, degree of fixation of the tissue, temperature of the block, temperature of the tissue, etc.) can affect the speed of sound. Although the density of the embedding material may impact sound speeds, TOF measurements may yield important information about tissue properties, tissue fixation state, the impregnating process used to embed the tissue, or the like. The contribution to the sound speed by the tissue can be isolated out from the contribution to the sound speed of the embedding material to evaluate the properties of the tissue.

After analysis, the embedded specimen can be cut into mountable sections, placed on a microscope slide, and then dried. A microtome can cut the specimen into thin mountable sections, for example, slices on the order of about 5 microns to about 6 microns thick. Each section can include a portion of the tissue sample and some of the embedding material. Different techniques can be used to transfer the tissue specimens onto the microscope slide. In some embodiments, the cut sections are floated on water to spread or flatten the sections. If the sections are pieces of paraffin embedded tissue, the sections can be floated on a warm bath to keep the sections in generally flat configurations, thereby reducing or preventing folding, creasing, or bending. A microscope slide is inserted into the warm bath. A front surface of the slide is used to pick up the tissue specimens.

Reagents can be applied to the tissue specimens. The composition of the reagent, processing times, or volume of reagent can be selected based on the information obtained by the processing system 100. Staining protocols for the embedded tissue specimens can be selected with limited or substantially no known information about the tissue specimen 150. Even archived tissue specimens can be matched with suitable reagents. Reagents include, without limitation, stains, wetting agents, probes, antibodies (e.g., monoclonal antibodies, polyclonal antibodies, etc.), antigen recovering fluids (e.g., aqueous- or non-aqueous based antigen retrieval solutions, antigen recovering buffers, etc.), or the like. Stains include, without limitation, dyes, hematoxylin stains, eosin stains, conjugates of antibodies or nucleic acids with detectable labels such as haptens, enzymes or fluorescent moieties, or other types of substances for imparting color and/or for enhancing contrast.

The analyzer 114 can be used to determine whether the specimen 150 has been fixed and, if so, the degree of fixation. If the specimen 150 has not been fixed, the specimen 150 can be fixed. If the specimen 150 is properly fixed, the specimen 150 can be removed from the fixative bath or the fixative can be deactivated. Deactivation of the fixative 170 can be achieved by diluting the fixative, exchanging fluids, rendering the fixative inactive, or the like.

If the specimen 150 has been left in the fixative 170 for an extended period of time, it may be fixed. Specimens are often inadvertently left in fixatives, for example, overnight. In such cases, the specimen may not need any additional fixing. The analyzer 114 can analyze the characteristic sound speeds of the specimen 150 and compare the measured characteristic sound speed to a typical sound speed for the tissue type of the specimen 150. Based on the comparison, the computing device 160 can determine the degree of fixation, if any, of the specimen 150. For example, if the sound speed does not change a threshold amount within an expected time frame, the specimen 150 is already fixed. Thus, the specimen 150 can be removed from the fixation bath or the fixation process can be stopped to avoid overfixation. By way of another example, the measured characteristics can be compared to stored values (e.g., sound speed characteristics of fixed tissue) to determine the degree of fixation. If the specimen 150 is already fixed, the characteristic sound speed will correspond to the sound speed of fixed tissue.

Figure 17:
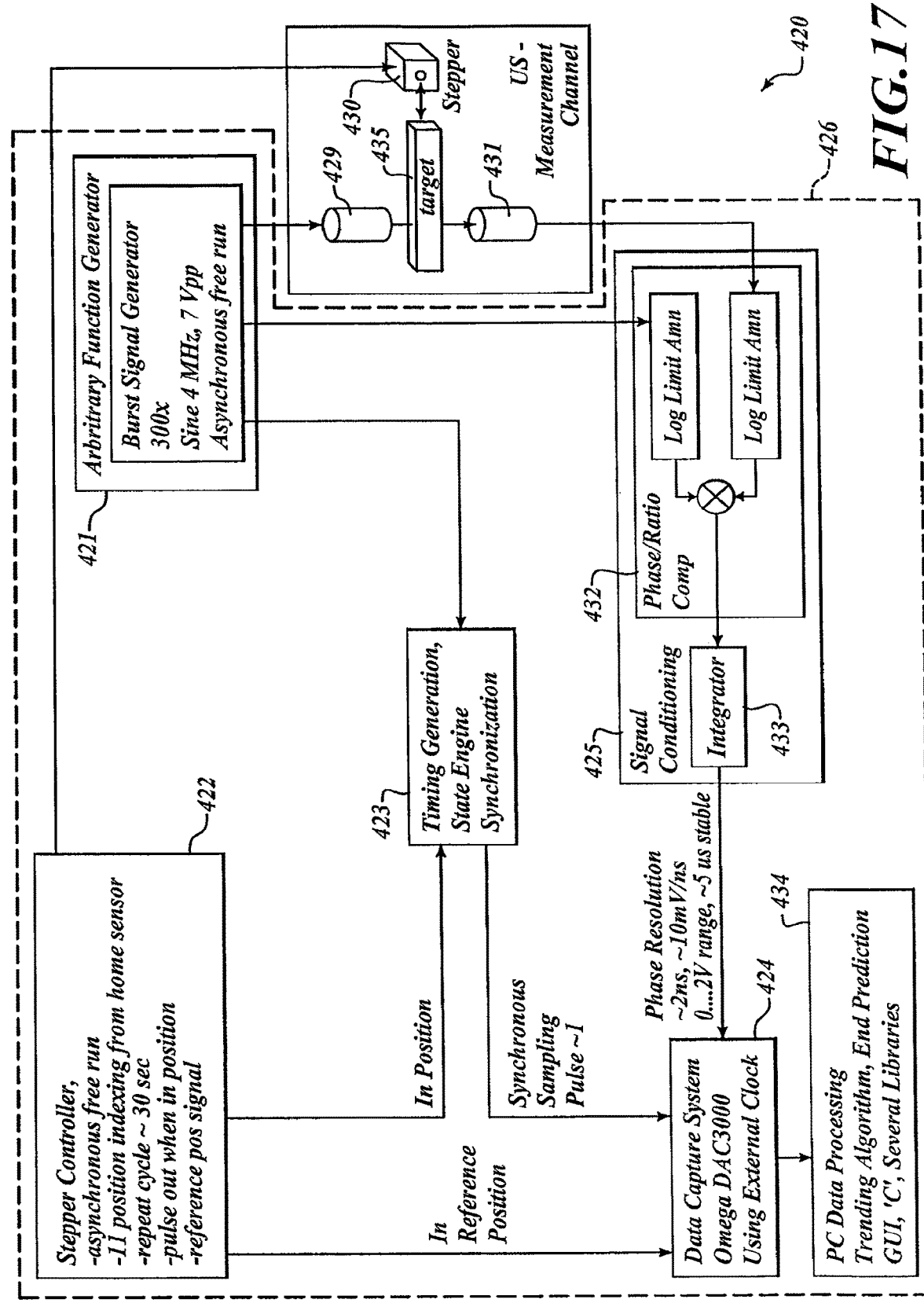
FIG. 17 is a block diagram of a processing system, in accordance with one embodiment.

FIG. 17 shows a processing system 420 with a computing device 426 configured to perform signal comparison by, for example, capturing and analyzing ultrasound phase velocity changes. The computing device 426 can monitor perfusion, thermal equilibration, alcohol contraction, evaporation, fixation, combinations thereof, or the like. The computing device 420 is similar to the computing device 160 discussed in connection with FIG. 3, except as detailed below.

A function generator 421 can send signals to a synchronization device 423 and to a transmitter 429. A controller 422 sends signals to the synchronization device 423 and to a positioning mechanism 430. The positioning mechanism 430 positions a sample between the transmitter 429 and a receiver 431 based, at least in part, on the signals from the controller 422.

The synchronization device 423 can synchronize signals based on phase shifts, outputted/received frequencies, signal comparisons, or the like and outputs signals to a capture system 424. The capture system 424 can be a data capture system the relies on an internal or external clock. In some embodiments, the capture system 424 can be an Omega DAC 3000 sold by Omega Engineering, Inc. or similar type of device. Other types of capture systems can also be utilized, if needed or desired.

A signal conditioner 425 receives output from the function generator 421 and output from the receiver 431. An analog or digital phase/ratio comparator 432 outputs signals to an integrator 433 (e.g., a digital integrator, an analog integrator, etc.), which in turn outputs signals to the capture system 424. The signal conditioner 425 can include other components, circuits, signal processing units such as DSPs, FPGAs, digital-to-analog devices, analog-to-digital devices, amplifiers (e.g., gain amplifiers), RF/IF gain phase detectors, or the like.

A computing unit 434 receives signals from the capture system 424 and can include frequency/phase shift databases for correlating phase shifts or convolutions for chirped pulse excitation to fixation states, control maps, fixation data, protocols, or the like. The computing unit 434 can control the components of the computing system 420. By way of example, the function generator 421 and the controller 422 can be controlled to automatically monitor and process the specimen 435.

The system 420 can perform ultrasound velocity measurements based on phase differences observed between transmitted pulse packet (e.g., 100-300 waves of constant wavelength) and received pulse packet after exposure to the sample tissue 435. The phase differences can be measured as an absolute phase angle difference relative to the wavelength of the base frequency of the pulse packet (e.g., 0 degrees to 360 degrees).

Figure 18:
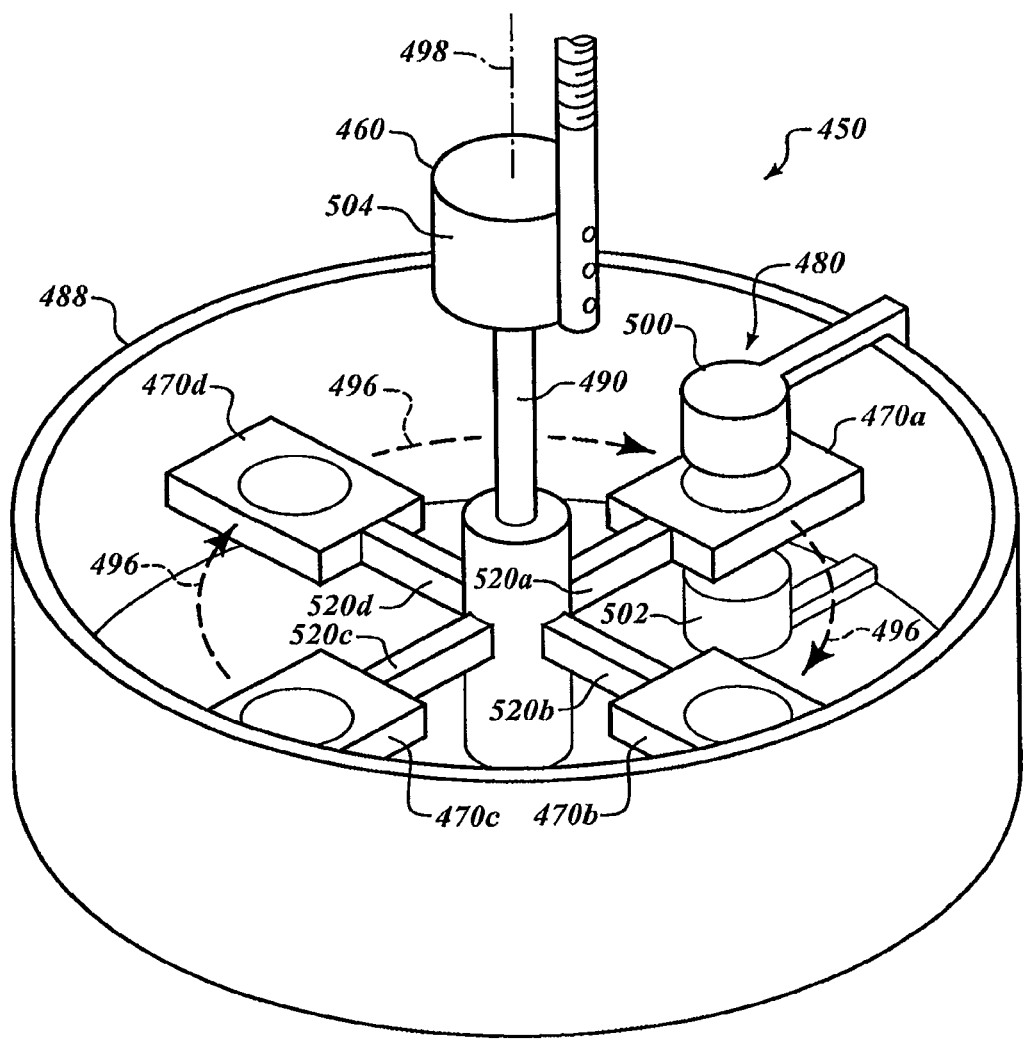
FIG. 18 is an isometric view of a processing system capable of sequentially analyzing specimens.

FIG. 18 shows a processing system 450 that includes a transport apparatus 460 configured to successively move specimen holders 470a, 470b, 470c, 470d (collectively 470) to an analyzer 480. The transport apparatus 460 includes arms 520a, 520b, 520c, 520d (collectively 520) that extend outwardly from a member 490. The specimen holders 470 are carried by the respective arms 520. The specimen holder 470a is shown in the analyzer 480. To move the specimen holder 470d into the analyzer 480, the member 490 is rotated (e.g., in a clockwise direction indicated by arrows 496) about an axis of rotation 498 until the specimen holder 470d is between a transmitter 500 and a receiver 502 of the analyzer 480. A positioning mechanism in the form of a drive motor 504 can rotate the member 490 based on feedback from the analyzer 480. A computing device, for example, can control the motor 504 in response to signals from the analyzer 480. The motor 504 can be a drive motor, stepper motor, or the like.

A fixative (not shown in FIG. 18) held in a container 488 can fix the specimens in the specimen holders 470. Advantageously, when a path between the transmitter 500 and the receiver 502 is unobstructed, the acoustic characteristics of the media can be evaluated to determine any changes in sound speed due to the media. The processing system 100 can then be recalibrated. If the distance between the transmitter 500 and the receiver 502 is about 50 millimeters, signals can be sent every few milliseconds because the total travel time may be about 40 µs. The frequency of transmitted acoustic energy, focal properties of transmitters, and geometry and dimensions of the transmitters can be selected to achieve a desired total travel time. Any number of signals can be sent at regular or irregular intervals to determine any processing changes that may affect the collected data.

The specimens can be individually monitored while all of the specimens undergo fixation. The processing system 450 can also have any number of analyzers 480. For example, the processing system 450 can have analyzers that are spaced apart from each other such that the specimen holders 470 are successively delivered to the analyzers. The analyzers may have different types of components to evaluate different properties of the specimens.

Figure 19:
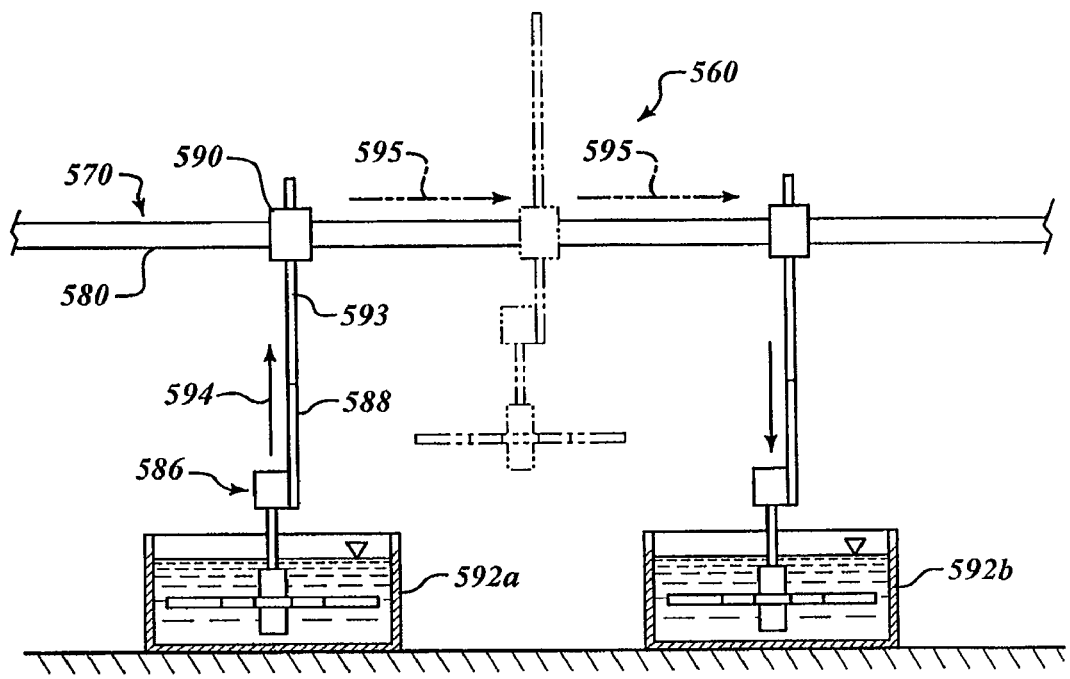
FIG. 19 is an elevated, partial cross-sectional view of a processing system capable of performing multiple treatments on specimens, in accordance with one embodiment.

FIG. 19 shows a processing system 560 for automatically processing specimens in different fluids. The samples can be processed in batches such that each batch of specimens is processed using the same protocol. The system 560 includes a drive apparatus 570 with a rail 580 and a transport apparatus 586 movable along the rail 580. The transport apparatus 586 includes a vertically movable rod 588 connected to a carriage 590. The carriage 590 can slide along the rail 580 to move the transport apparatus 586 between containers 592a, 592b.

To move the illustrated transport apparatus 586 to the container 592b, the carriage 590 raises the transport apparatus 586 from a lowered position 593, as indicated by an arrow 594. Once the transport apparatus 586 is out of the container 592a, the carriage 590 can move along the rail 580, as indicated by arrows 595. Once the raised transport apparatus 586 is above the container 592b, the carriage 590 lowers the transport apparatus 586 into the container 592b. In this manner, specimen holders carried by the transport apparatus 586 can be submerged in processing media in the containers 592a, 592b. In some embodiments, including the illustrated embodiment, the container 592a contains a fixative, and the processing media in the container 592b is a clearing agent.

Figure 20:
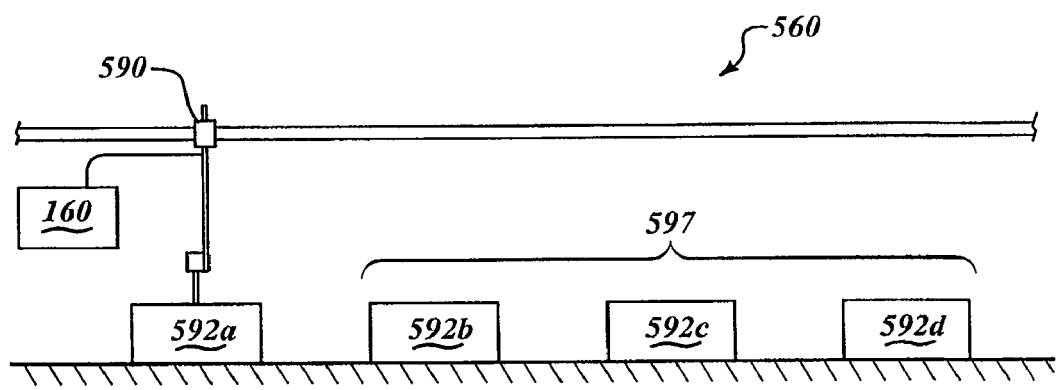
FIG. 20 is a side elevational view of a processing system capable of performing multiple treatments on specimens, in accordance with one embodiment.

Any number of containers can be used with the illustrated processing system 560. FIG. 20 shows a modified embodiment of the processing system 560 with containers 592a, 592b, 592c, 592d (collectively 592). A carriage 590 can carry the specimens sequentially into the containers 592, which can contain a wide range of different types of processing medias, including fixatives, clearing agents (e.g., xyline or the like), infiltrations, dehydration agents, reagents, or the like. The illustrated processing system 560 includes a tissue preparation unit 597 comprising the containers 592b, 592c, 592d.

The container 592a can contain a fixative in which specimens are fixed. After fixing, the specimens can be sequentially delivered to the containers 592b, 592c, 592d which each contain a tissue preparation media, such as a dehydration agent, a clearing agent, an infiltration agent, or the like. In some embodiments, the computing device 160 can generate a tissue preparation protocol used to process the specimens in the container 592b, which contains a dehydration agent, such as alcohol. The tissue specimen can be treated with a clearing agent in the container 592c. The specimen can be treated with an infiltration agent in the container 592d. The tissue preparation protocol can include length of processing times in the processing media, composition of the processing media, temperature of the processing media, or the like. Of course, different specimens with different types of tissue, dimensions, etc. can be processed for different lengths of time. As such, different tissue preparation protocols can be generated for different tissue types to ensure that the specimens are adequately prepared for embedding.

Figure 21:
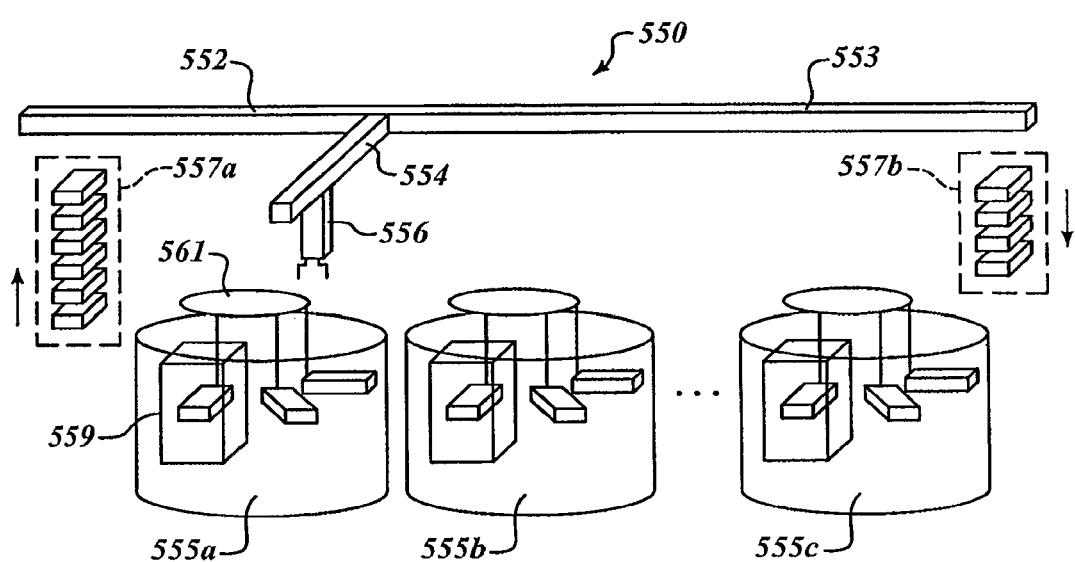
FIG. 21 is a side elevational view of a processing system capable of individually processing tissue specimens.

FIG. 21 shows a processing system 550 for automatically processing specimens and random access loading. STAT processing can reduce the time to diagnosis for high priority samples. The processing system 550 includes a drive apparatus 552 with a rail 553 and a handing device, illustrated as a 3-axis handling robot 554, movable along the rail 553. The 3-axis handling robot 554 includes a lifter 556 for transporting specimen holders to stations, illustrated as containers 555a, 555b, 555c (collectively 555). Specimen holders can be loaded at any time from a feed mechanism 557a (illustrated in dashed line) to the container 555a. Each container 555 includes a rotary positioning mechanism 561 for sequentially positioning specimens in a channel of an analyzer 559. The specimens can be monitored to ensure proper fixation. New samples can be automatically loaded at any time. In contrast to the batch operations discussed in connection with FIGS. 18-20, once a specimen is processed, it can be removed from the container while other specimens are processed.

Specimen holders can be placed in the first processing container 555a holding cold formalin or warm formalin. The specimens can be sequentially fed through a measurement channel (e.g., an ultrasound TOF measurement channel) in order to track the progression of the reaction in the container 555a. Once a tissue sample process is complete, the handling robot 554 can remove the specimen holder with the processed sample and move it to the next processing station 555b. The individual handling of specimen holders can allow faster fixing of samples to be moved earlier and bypassing of slower fixing samples, thereby providing custom processing times optimized per individual sample. This increases the total throughput of the system 550.

By way of example, one specimen holder carrying a fatty tissue can be processed using a fatty tissue preparation protocol and another specimen holder carrying muscle tissue can be processed using a muscle tissue preparation protocol. The different protocols can provide different processing times, different waves (e.g., different frequencies, different waveforms, etc.), different compensation algorithms, or the like. A protocol can be selected based on individual sample treatment requirements due to size variations, type of tissue sample, history of tissue samples, and/or other characteristics of samples. If the size/material of sample changes, another protocol can be selected by the operator and/or automatically selected by a computing system.

Information collected from samples can be used for processing subsequent samples. Processing time information obtained from a sample can be used to determine a priori the processing times for the next station or monitoring (e.g., ultrasound TOF monitoring). The specimen holder can include information (e.g., machine-readable code) readably by readers at the containers 555a-c. Once processing is complete, the samples may be infused with paraffin and can be unloaded into an output queue 557b. The processed specimens can be picked up at convenient times.

Figure 22:
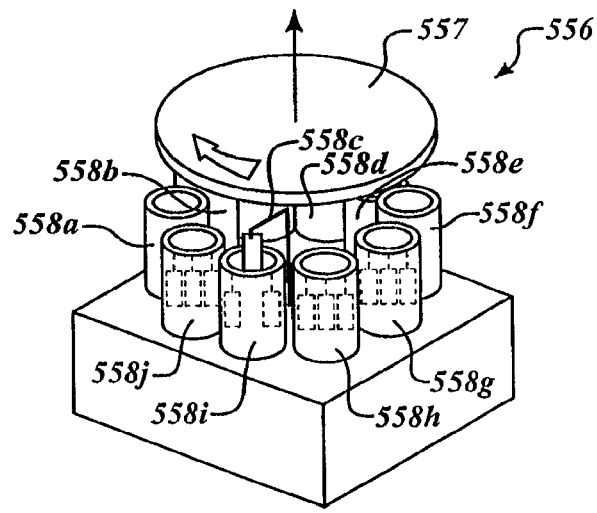
FIG. 22 is an isometric view of an analyzer with a rotary drive system.

FIG. 22 shows a processing system 556 that provides random access to tissue specimens. The processing system 556 includes a carousel positioning mechanism 557. A lifter 558 can grip and carry specimen holders or specimens between processing stations 558a-j, illustrated as open containers.

Figure 23:
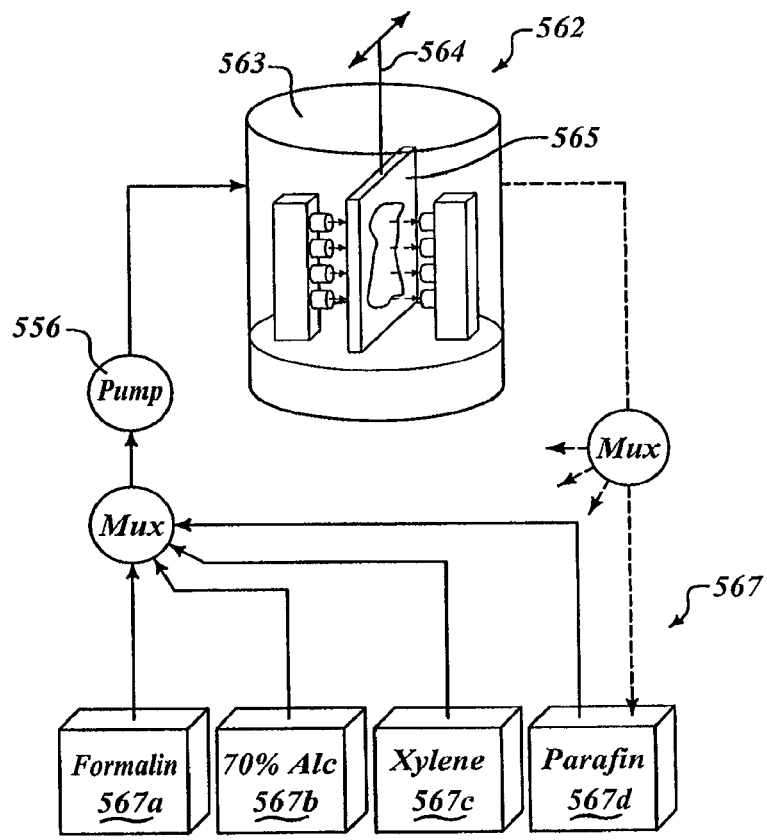
FIG. 23 is a processing system capable of fixing and embedding a tissue specimen.

FIG. 23 shows a station 562 with a single closed reaction chamber 563 and a positioning system in the form of a mechanical drive mechanism 564. A pump 566 can exchange media. A valve/multiplexer system 567 fluidically couples containers 567a-d. Additionally or alternatively, one or more vacuum devices can be used to transport fluids between containers. Any number of multiplexer pumps, valve systems, vacuum devices, conduits, thermal devices, containers, or other fluid devices can be used to manage processing media.

Figure 24:
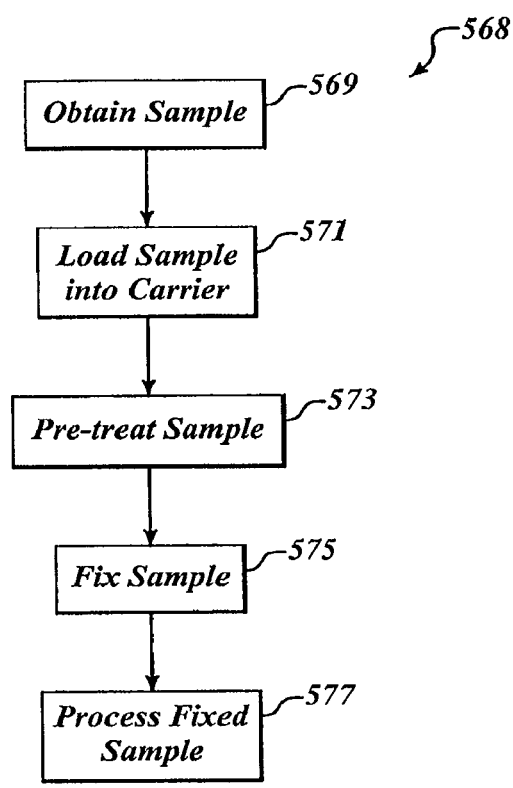
FIG. 24 is a flow diagram of an exemplary method of processing a specimen.

FIG. 24 is a flow chart of a workflow system 568. Generally, the workflow system 568 is used to track samples with the corresponding subject identification from surgery through tissue processing. Information obtained from the samples can be included in the subject's records and can facilitate generation of reports (e.g., reports used for diagnosis, patient monitoring, billing, etc.), an audit trail (e.g., an audit trail of specimen handling steps), a processing parameter log (e.g., a log that could be printed and as a quality record at the end of the processing), or the like.

Samples can be monitored by an active (or passive) RFID tag embedded in or otherwise coupled to the specimen holder. Once the sample is acquired, it can be transferred to the specific specimen holder. In some protocols, the specimen can be stored in a cooled container (−4° C.) with 10% neutral buffered formalin by volume. Upon entry into the specimen holder and container, the RFID tag can be programmed, such as by swiping past a communication device (e.g., reader/writer device) to track the time and allow association of the patient ID to the unique RFID device ID. Alternatively, a bar coding scheme with a linked database or other machine-readable code could be used, if needed or desired.

At 569, a sample is taken from a subject. The sample can be a tissue sample removed from a subject using a needle, biopsy tool, or the like and can be a section of tissue, an organ, a tumor section, a smear, a frozen section, a cytology prep, or cell lines. An incisional biopsy, a core biopsy, an excisional biopsy, a needle aspiration biopsy, a core needle biopsy, a stereotactic biopsy, an open biopsy, or a surgical biopsy can also be used to obtain the sample.

At 571, the sample is loaded into a specimen holder with machine-readable code. The machine-readable code can be any type of optical symbology, magnetic pattern or electromagnetic or electrostatic signal having information content. For example, information content may relate to sample identity, sample origin, sample chain of custody, instructions for processing a sample, information regarding the characteristics of a sample, test results for a sample, images of the sample and the like.

The workflow system 568 can include any number of communication devices capable of reading and/or writing information. A communication device can be any type of machine that can decipher, translate or interpret the information contained in a machine-readable code, for example, a device that converts the code into commands for performing an automated procedure or presenting the information in a human-readable or human-interpretable form. A communication device can be a reader compatible with one or more different types of machine-readable code, such as optical symbologies, bar codes, and the like. Examples of optical symbologies include characters, bar codes and dataglyphs. Particular examples of bar codes include linear bar codes, multi-dimensional bar codes such as 2D stacked symbologies and 2D matrix symbologies, and composite bar codes such as reduced-space symbologies. Even more particular examples of 2D optical symbologies include PDF417, data matrix, maxicode, vericode, codablock, aztec code, code 16K and QR code. Bar code readers for these and any number of other optical symbologies are well known. Where the machine-readable code comprises characters (e.g., alphanumeric characters such as English text and Arabic numbers) the code reader can be an optical character reader (OCR). Magnetic stripes are only one example of a device that can store information in the form of a magnetic pattern. An example of an electromagnetic code is an RFID tag. RFID tags typically include a small metallic antenna and a silicon chip, and can be active or passive. RFID code readers are well known, and typically include an antenna and a transceiver that receives information from the RFID tag. The information content of an RFID tag can be fixed or changeable. In another embodiment, the communication device is a code reader that includes a CCD camera and the CCD camera can be used for simultaneous detection of samples and reading of a bar code or characters. Other examples of machine-readable codes that can be used include Bragg-diffraction gratings and micro- or nano-bar codes (such as spatial and spectral patterns of fluorescent particles or spatial patterns of magnetic particles).

At 573, the sample can be pretreated to facilitate subsequent processing. The sample can be pre-treated with formalin or other media. Pre-treatments are discussed in connection with FIGS. 39-42.

At 575, the sample can be delivered to a processing system and undergoes a fixation process. A user can select the configuration based on the configuration of the processing system. The sample can be monitored during fixation. Processing times, fixation history, tissue characteristics, or other histology information can be used to adjust processing to ensure proper histology tissue processing.

At 577, the tissue can be prepared for examination or storage. The sample can be embedded, sectioned, and transferred onto a microscope slide for subsequent processing and analyses, such as staining, immunohistochemistry, or in situ hybridization. To section a tissue sample for optical microscope examination, a relatively thin strip of tissue can be cut from a large tissue sample so that light may be transmitted through the thin strip of tissue. A microtome can cut the specimen into thin sections, for example, slices on the order of about 5 microns to about 6 microns thick. Each section can include a portion of the tissue sample and some of the embedding material. The microtome and any other equipment (e.g., a staining station, an embedding station, an oven, etc.) used in the system 556 can include communication devices to read and/or write information to the specimen holder.

The tissue specimen can be transferred onto a microscope slide, which can include machine-readable code. In some embodiments, the cut sections are floated on water to spread or flatten the sections. If the sections are pieces of paraffin embedded tissue, the sections can be floated on a warm bath to keep the sections in generally flat configurations, thereby reducing or preventing folding, creasing, or bending. A microscope slide is inserted into the warm bath. A front surface of the slide is used to pick up the tissue specimens. To examine multiple tissue samples (e.g., a set of tissue samples, each taken at a different location in a subject) using a single slide, a plurality of the tissue samples may be sequentially floated onto the slide. These wet slides are then dried using the slide dryer and coverslipped.

Figure 25:
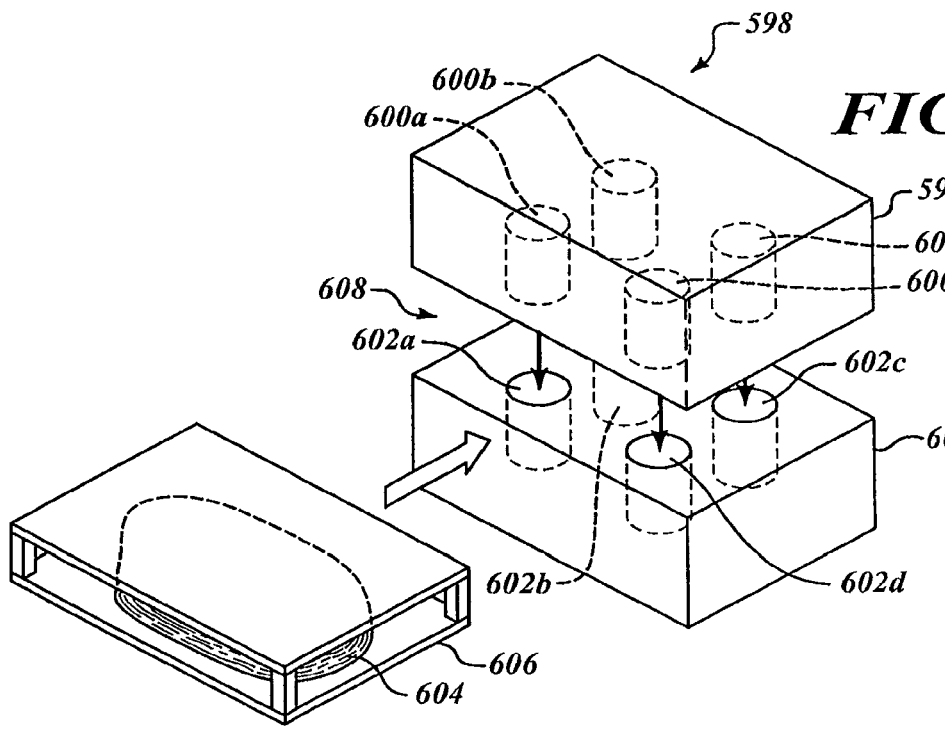
FIG. 25 is an isometric view of an analyzer ready to receive a specimen holder.

FIG. 25 shows an analyzer 598 that includes a transmitter unit 599 with an array of transmitters 600a, 600b, 600c, 600d (collectively 600) and a receiver unit 601 with an array of receivers 602a, 602b, 602c, 602d (collectively 602). Transmitters 600 are aligned with respective receivers 602. The pairs of transmitters 600 and receivers 602 can monitor different sections of a specimen 604. The number of transmitters/receivers, positions of the transmitters/receivers, and the spatial resolution of the analyzer 598 can be selected based on the size of the specimen 604. In order to expand the spatial resolution for relatively small biopsy cores, the focal diameters of the transmitters 600 can be relatively small. In certain embodiments, the focal diameters can be in a range of about 2 millimeters to about 5 millimeters. Other ranges of focal diameters are also possible. Other means of adjusting the focal properties may include, without limitation, acoustic lenses or apertures in front of the transmitters/receivers. The focal diameters of the transmitters 600 can overlap to ensure that the entire specimen 604 is analyzed. In other embodiments, the focal diameters of the transmitters 600 can be spaced apart from one another.

To analyze the specimen 604, a specimen holder 606 can be moved through a gap 608 between the transmitter unit 599 and the receiver unit 601. In some embodiments, the specimen holder 606 is moved through the gap 608 using a transport apparatus. In other embodiments, the specimen holder 606 is manually inserted into the gap 608.

Figure 26:
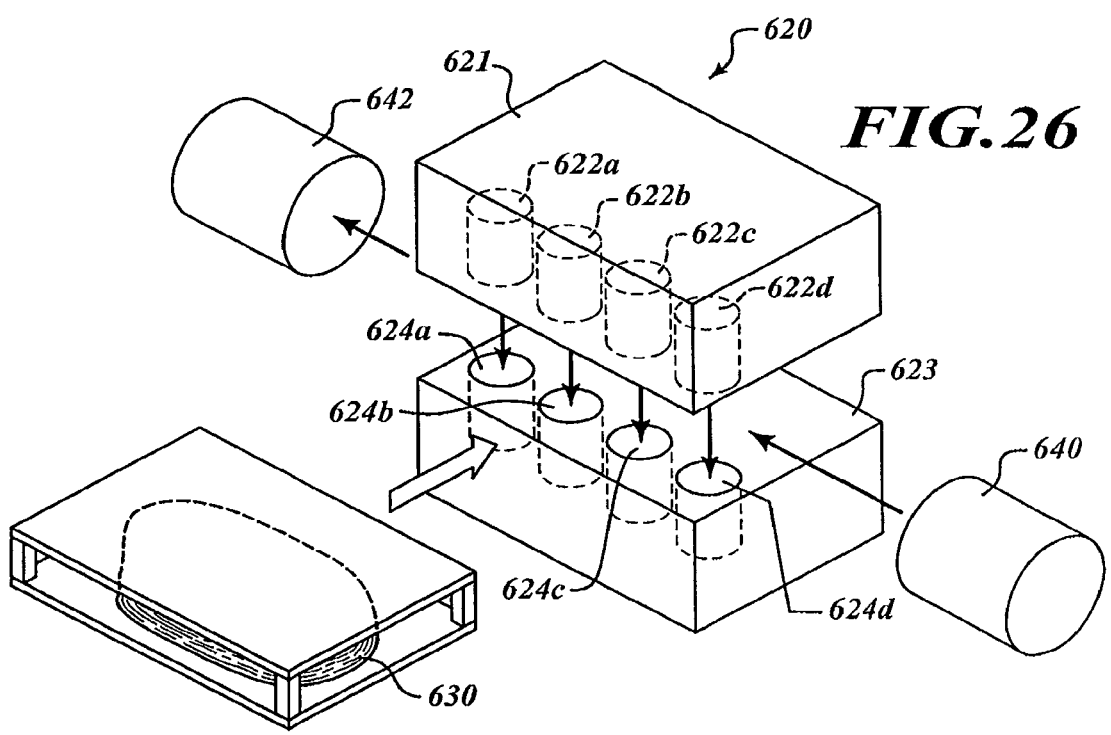
FIG. 26 is an isometric view of an analyzer with a linear array of transmitters and a linear array of receivers.

FIG. 26 shows an analyzer 620 with a transmitter unit 621 and a receiver unit 623. The transmitter unit 621 includes transmitters 622a, 622b, 622c, 622d (collectively 622). The receiver unit 623 includes receivers 624a, 624b, 624c, 624d (collectively 624). The illustrated linear array of transmitters 622 and linear array of receivers 624 can scan a specimen 630.

Different combinations of transmitters and receivers can be used to provide different sound paths through tissue specimens. As shown, a transmitter 640 can communicate with a receiver 642 such that the sound paths between the transmitters 622 and receivers 624 is generally perpendicular to a sound path between the transmitter 640 and the receiver 642. Thus, measurements can be taken in different directions. Such embodiments are well suited for analyzing specimens with anisotropic properties. The number, types, orientations, and positions of transmitters/receivers can be selected based on the characteristics of the specimen.

Figure 27:
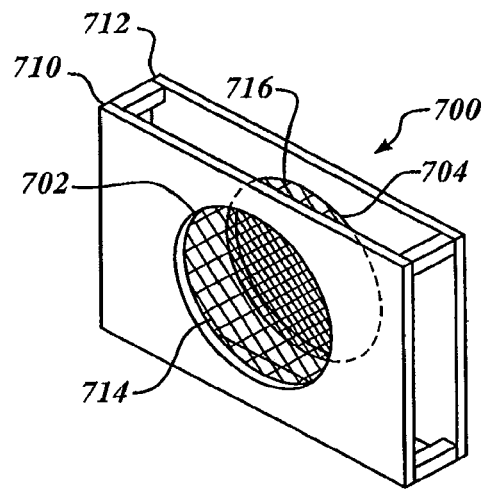
FIG. 27 is an isometric view of a specimen holder, in accordance with one embodiment.

FIG. 27 shows a specimen holder 700 that includes plates 710, 712 that are spaced apart and generally parallel to one another. Apertures 702, 704 facilitate delivery of acoustic waves to a tissue specimen. A specimen can be sandwiched between the plates 710, 712 and held in a substantially flat configuration. Acoustic energy can travel generally perpendicular to the plates 710, 712 and can pass through the aligned apertures 702, 704.

Barrier elements 714, 716 can block the apertures 702, 704, respectively. Each of the barrier elements 714, 716 can include, without limitation, a mesh, a perforated material, a web, a grate, a screen, foil, fabric, or any other structure or material through which acoustic waves can travel with minimal, limited, or substantially no attenuation. The barrier elements 714, 716 can thus keep the specimen within the specimen holder 700. The barrier elements 714, 716 can also be permeable to ensure that a sufficient amount of the specimen is contacted by the processing media. In some embodiments commercially available biopsy tissue cassettes may be utilized.

Figure 28:
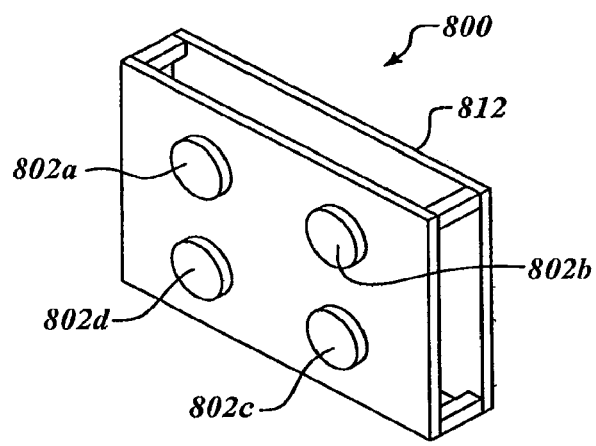
FIG. 28 is an isometric view of a specimen holder with transmitters and receivers.
Figure 29:
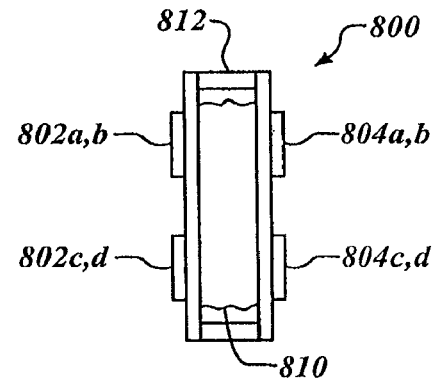
FIG. 29 is a side elevational view of the specimen holder of FIG. 28.

FIGS. 28 and 29 show a specimen holder 800 that is generally similar to the specimen holder 700, except as detailed below. FIG. 29 shows the specimen holder 800 holding a specimen 810. The specimen holder 800 includes transmitters 802a, 802b, 802c, 802d (collectively 802) and receivers 804a, 804b, 804c, 804d (collectively 804). The transmitters 802 and receivers 804 can contact or be proximate to the specimen 810 to minimize signal attenuation and other problems often associated with transmitting across relatively large distances, and to minimize or limit attenuation attributable to processing media (e.g., if a gap is formed between the specimen 810 and the walls of the holder 800).

The transmitters 802 and receivers 804 can be coupled to a main body 812. In certain embodiments, the transmitters 802 and receivers 804 are permanently coupled to or integrated into the main body 812. In other embodiments, the transmitters 802 and receivers 804 are removably coupled to the main body 812 to allow components to be interchanged or removed for inspection, maintenance, or the like. To facilitate physical contact between the specimen 810 and processing media, the specimen holder 800 can have any number of apertures and can be made of a permeable or semi-permeable material.

The tissue specimen holder 700 of FIG. 27 and the specimen tissue holder 800 of FIGS. 28 and 29 can be used with the processing system 100 of FIGS. 1 and 2, the processing system 450 of FIG. 18, the processing systems 560 of FIGS. 18-20, the processing system 550 of FIG. 21, etc. Processing systems can thus be configured to receive a wide range of different types of specimen holders with or without transmitters or receivers, sensors, apertures, or the like.

Figure 30:
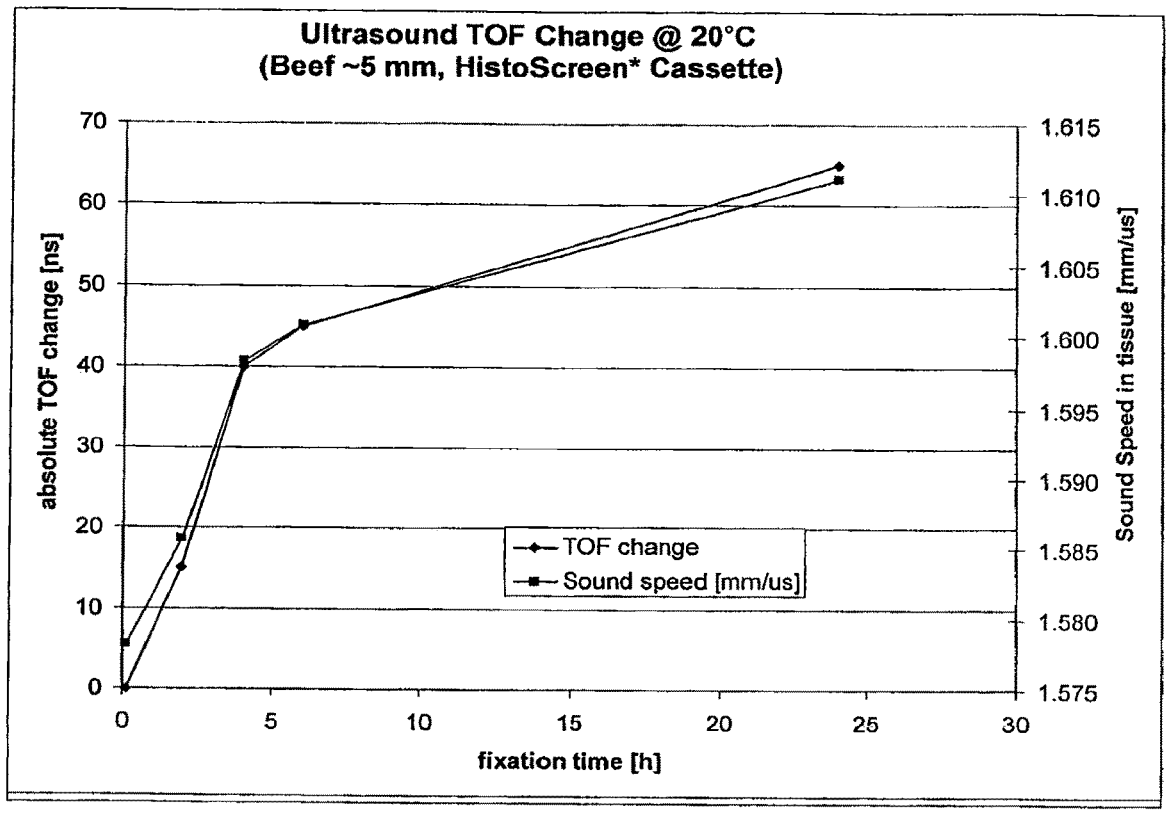
FIG. 30 is a plot of fixation time versus sound of speed in tissue and absolute TOF change for beef tissue.
Figure 31:
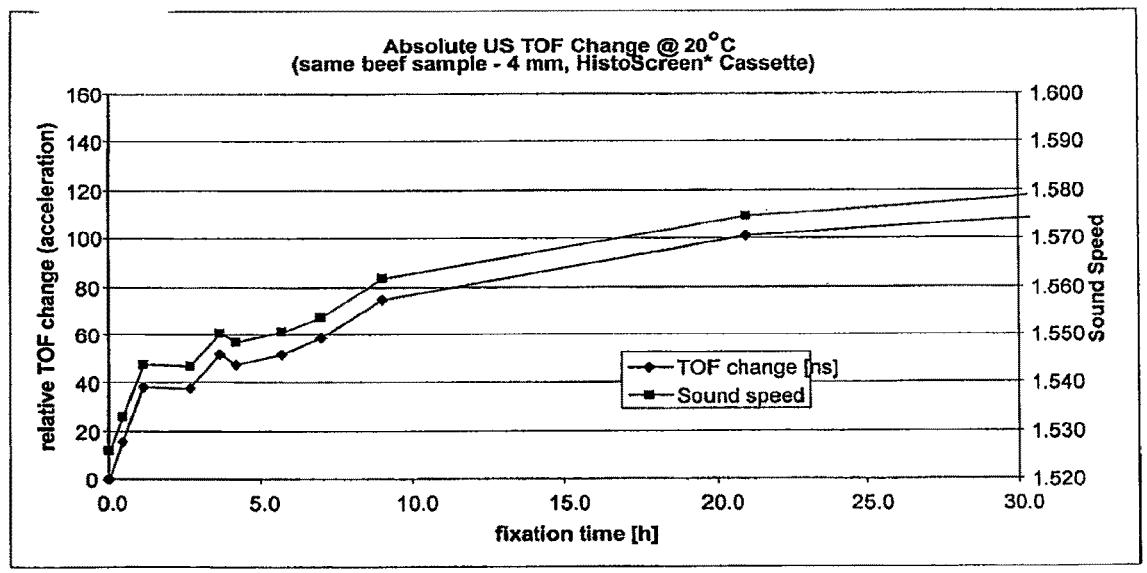
FIG. 31 is a plot of fixation time versus sound speed and relative TOF change for beef tissue.
Figure 34:
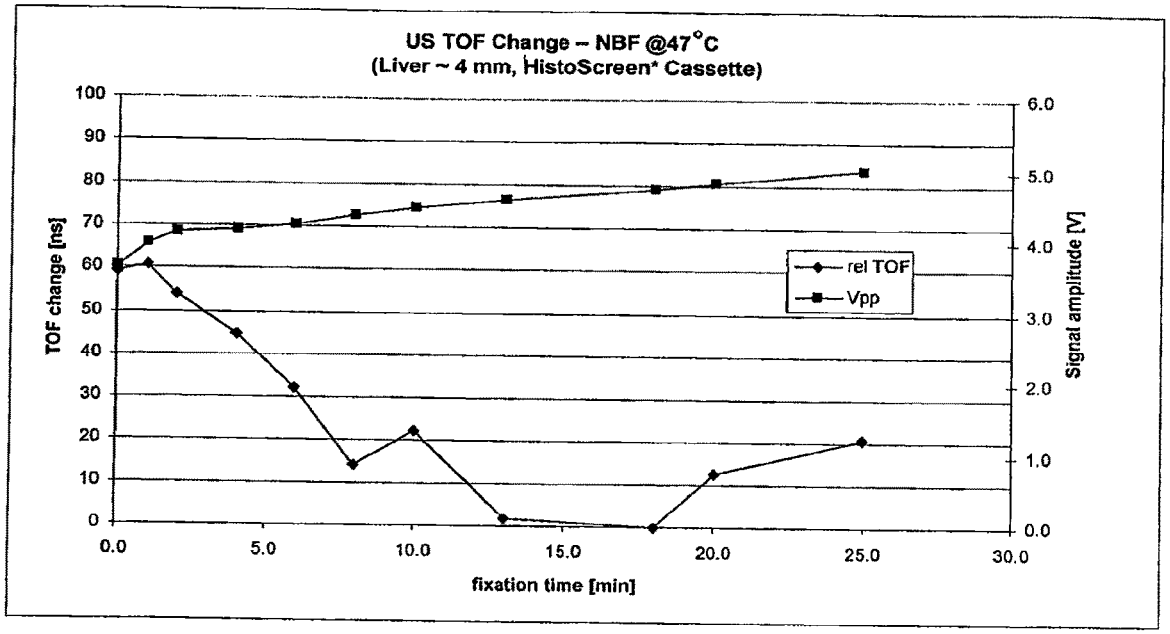
FIG. 34 is a plot of fixation time versus signal amplitude and TOF change for liver tissue.
Figure 35:
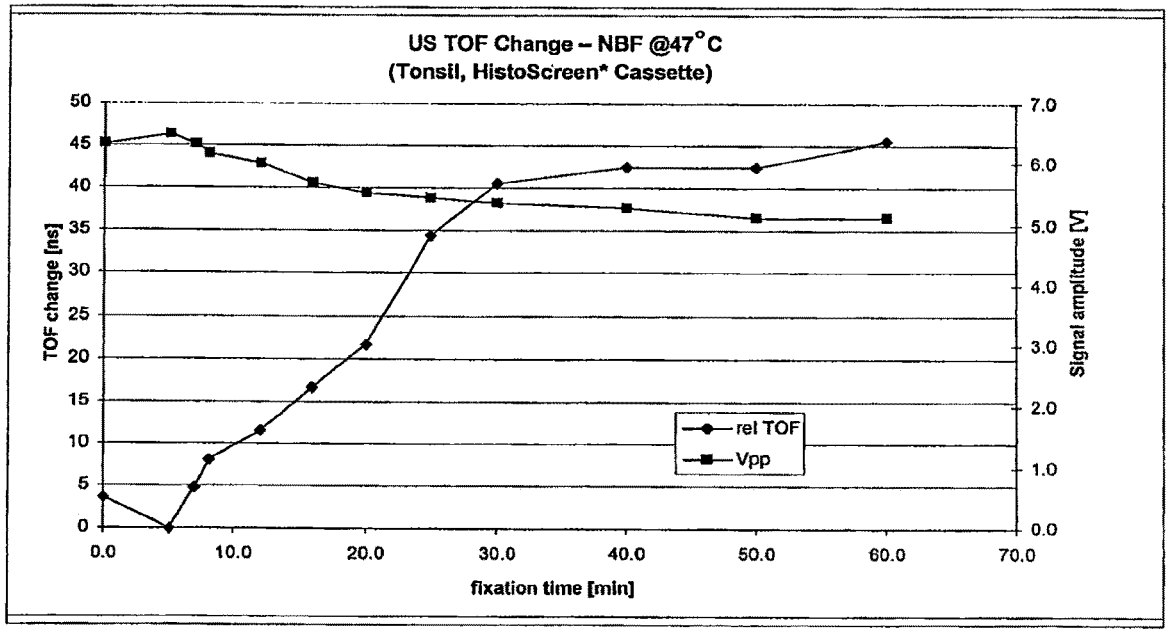
FIG. 35 is a plot of fixation time versus signal amplitude and TOF change of human tonsil tissue.
Figure 36:
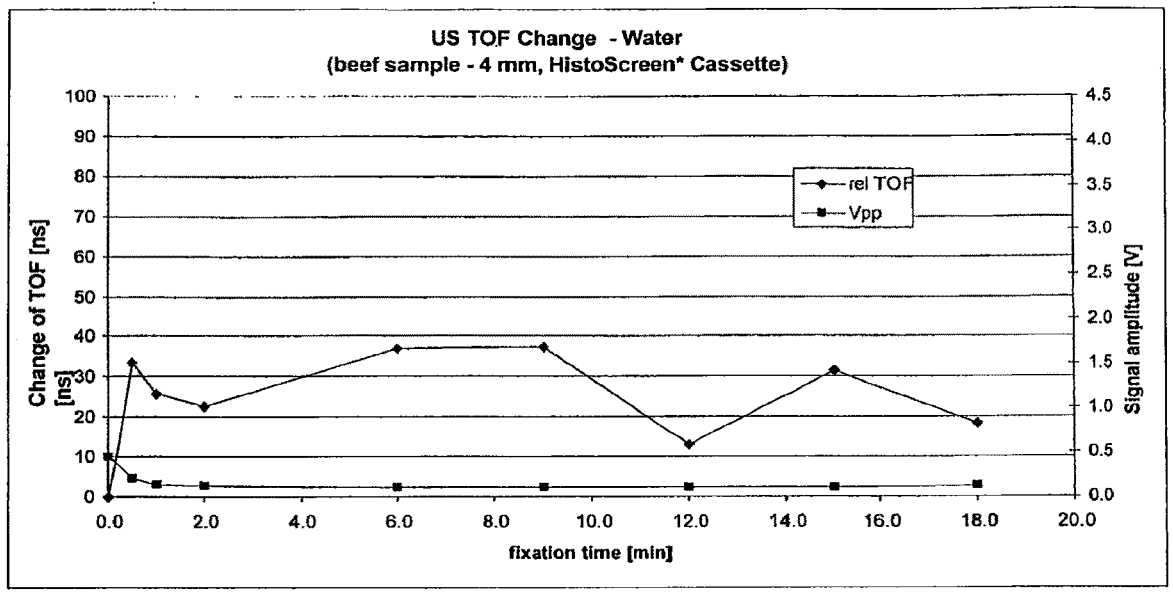
FIG. 36 is a plot of fixation time versus signal amplitude and TOF changes for beef tissue.

FIGS. 30-36 show measurements generated from a processing system analyzing specimens. FIGS. 30 and 31 show measurements taken with NBF at room temperature (e.g., about 20° C.). A heated bath of NBF was used to obtain the measurements of FIGS. 32-35. Heated baths can be used to reduce fixation times. FIG. 36 shows a negative control run in water.

Referring to FIG. 30, beef muscle was cut into approximately 4 mm to 5 mm thick pieces and fixed in time increments of about less than 1 hour, 2 hours, 4 hours, 6 hours, and 24 hours. TOF was measured while the fixative was kept at room temperature. As shown, equivalent sound speed change was observed from about 1,580 m/s to about 1,610 m/s.

FIG. 31 shows fixation time versus sound speed and relative TOF change. The measurements were obtained using a sample of beef muscle with a thickness of about 4 mm. Inline monitoring was used to monitor fixation in a bath of NBF for about 21 hours. Equivalent sound speed change was observed from about 1,520 m/s to about 1,580 m/s.

Figure 32:
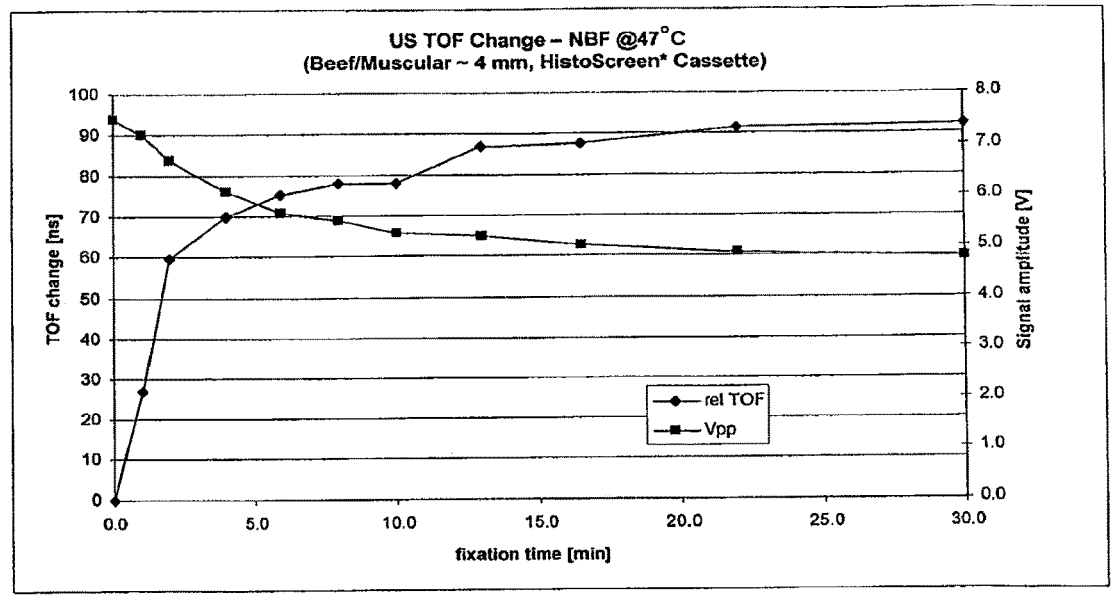
FIG. 32 is a plot of fixation time versus signal amplitude and TOF change for beef tissue.

FIG. 32 shows fixation time versus signal amplitude and TOF change in a heated bath of neutral buffered formalin (NBF). A tissue sample of beef muscle tissue was cut across its fibers. The tissue sample had a thickness of about 4 mm and was fixed in a heated bath of NBF. The NBF bath was kept at a temperature of about 47° C. with about +/−1° C. control.

Figure 33:
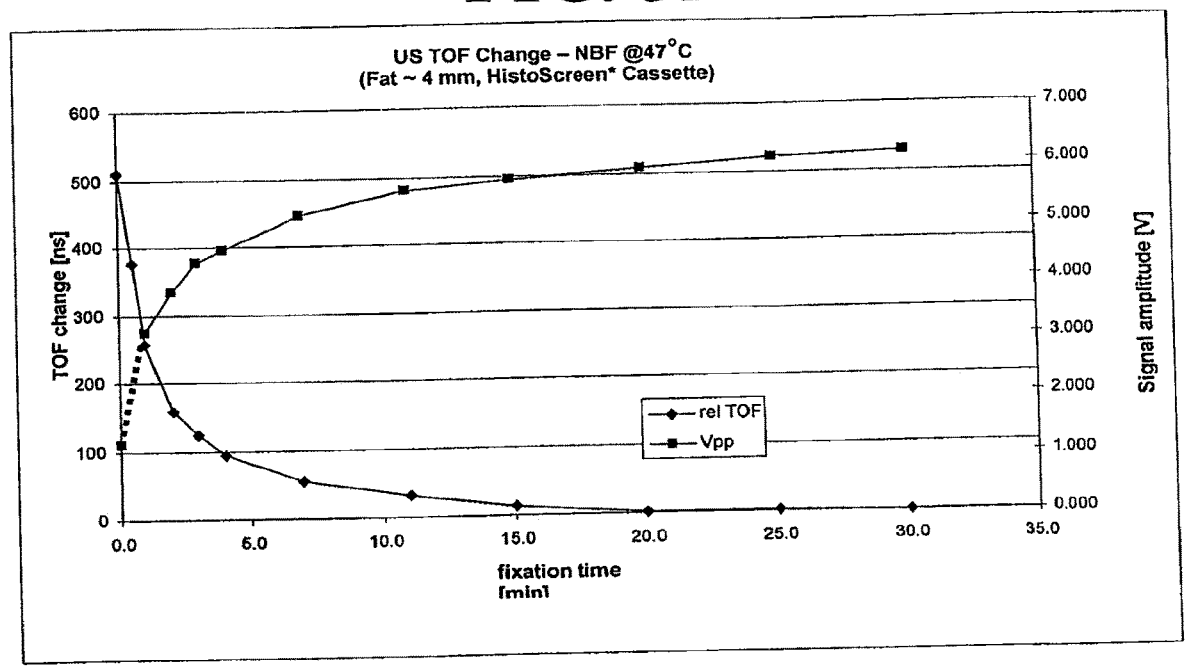
FIG. 33 is a plot of fixation time versus TOF change and signal amplitude for fat tissue.

FIG. 33 shows fixation time versus signal amplitude and TOF change of fat tissue in a heated bath of NBF. The fat tissue had a thickness of about 4 mm. The heated NBF bath was maintained at a temperature of about 47° C. with about +/−1° C. temperature control.

FIG. 34 shows fixation time versus signal amplitude and TOF change of liver tissue in a heated bath of NBF. A sample of liver tissue with a thickness of about 4 mm was fixed in the heated NBF bath maintained at about 47° C. with about +/−1° C. temperature control.

FIG. 35 shows fixation time versus signal amplitude and TOF change of human tonsil tissue in a heated bath of NBF. The tissue sample was fixed using a heated NBF bath maintained at about 47° C. with about +/−1° C. temperature control.

FIG. 36 shows fixation time versus signal amplitude and TOF change of muscular beef tissue in a negative control bath of deionized water. The tissue sample had a thickness of about 4 mm. The bath was heated and maintained at about 47° C. with about +/−1° C. temperature control.

Two protocols were used to analyze different types of tissue. In one protocol, different samples were fixed for different lengths of times and kept at about room temperature. Signal amplitude was measured in close succession. In the other protocol, the same samples were continuously monitored and kept at elevated temperatures until signal levels reached a plateau.

Both protocols produced similar results, with the elevated temperature processing providing faster fixation. The measurements (e.g., sound speed measurements) at higher temperatures are subject to more fluctuations due to temperature gradients in the media between the transmitter and the receiver and warm-up effects from the sample tissue and the specimen holder, which were initially introduced at room temperature and had to equilibrate. In another protocol, a specimen and specimen holder were briefly (e.g., about 5 minutes to about 10 minutes) warmed up externally to about 47° C. before being inserted into the measurement channel with similar results.

Figure 37:
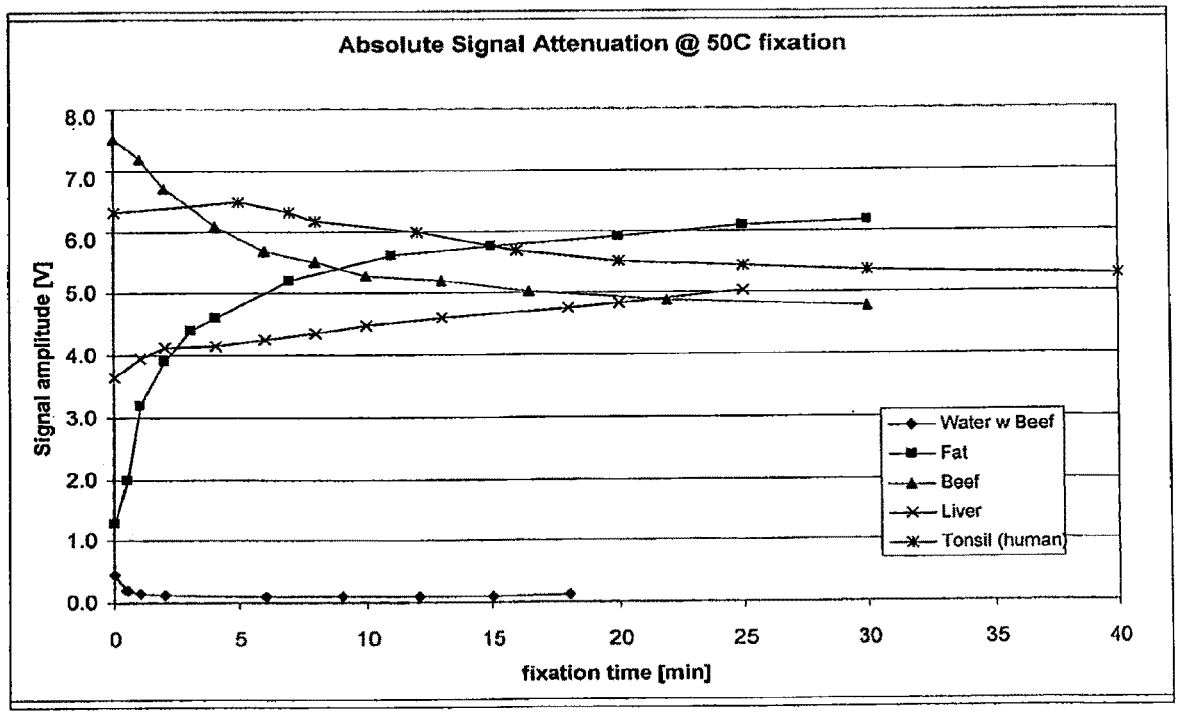
FIG. 37 is a plot of fixation time versus signal amplitude for different types of tissue.
Figure 38:
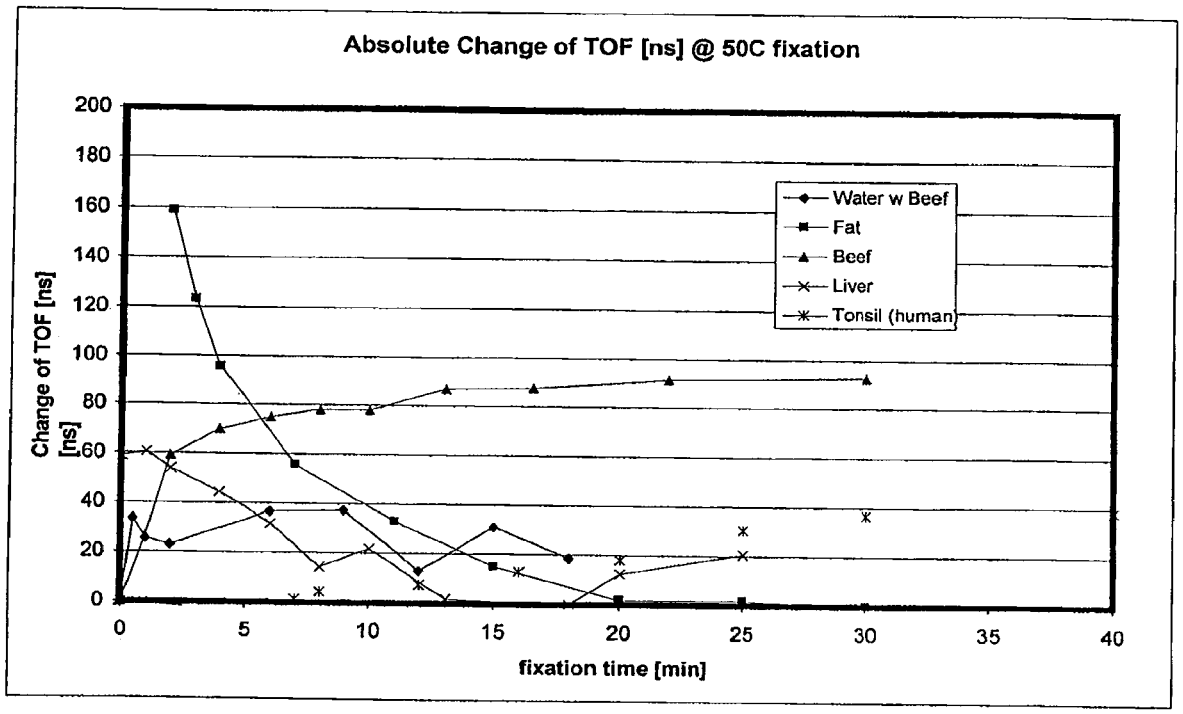
FIG. 38 is a plot of fixation time versus change of TOF for different types of tissues.

Results of TOF measurements and signal attenuation are shown in FIGS. 37 and 38 for comparison between different types of tissue. FIG. 37 shows fixation time versus signal amplitude for beef in water (which serves as a negative control) and fat, beef, liver, and tonsil in a fixative. The fixative was maintained at a temperature of about 5020 C. There is an increase of the received amplitude in fatty tissue. This may be due to better transmission capabilities, changes in density, combinations thereof, or the like due to the perfusion of the fixative and resulting cross-linking.

FIG. 38 shows fixation time versus change of TOF for different types of tissue maintained at about 50° C. The fatty tissue responded with exponential decay of the sound speed change during fixation. This may be because of a negative temperature coefficient of fat and the warming effects of the tissue due to elevated temperature testing. The muscular tissue responded with an exponential growth change of the sound speed mostly due to cross-linking. The growth change may also be increased due to elevated temperatures. FIGS. 30 and 31 show a similar increase of about 60 ns to about 100 ns (or about 60 m/s in sound speed) observed at room temperature, and may be related to fixation.

Table 2 below shows sound speeds in different types of specimens. The specimens had a thickness of 4 mm and were fixed with a fixative maintained at about 47° C.

TABLE 2

| Tissue type | Unfixed Speed at 47° C. [m/s] | Fixed Speed at 47° C. [m/s] | Sound speed change [m/s] | Signal Amplitude Change [%] |
| --- | --- | --- | --- | --- |
| Fat (beef) | 1,687 | 1,387 | −308 | +381% |
| Muscle (beef) | 1,618 | 1,681 | +63 | −58% |
| Liver (calf) | 1,767 | 1,737 | −30 | −38% |
| Tonsil (human) | 1,672 | 1,702 | +30 | +27% |

If the tissue type of a specimen is known, the sound speed changes (e.g., increases in sound speed, decreases in sound speed, or combinations thereof) can be used to determine the tissue type. For example, if a specimen of an unknown tissue type has an unfixed speed of about 1,687 m/s and the sound speed which decreases as the tissue is fixed, it can be concluded that the tissue may be fat tissue from beef. Of course, the unfixed sound speed of the tissue can be compared to the fixed sound speed to determine the tissue type with a high degree of accuracy. Different types of tissue samples have different characteristic sound speeds.

Figure 39:
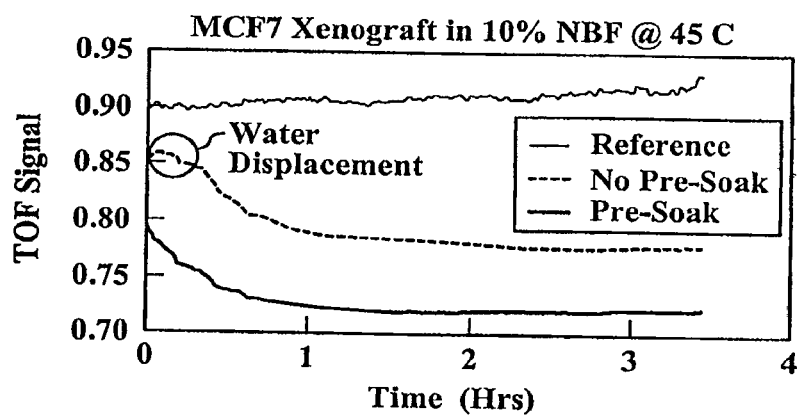
FIG. 39 is a plot of time versus a time of flight signal for a presoaked sample and a fresh sample.

Samples can be pre-treated to facilitate fixation (e.g., enhance fixation consistency, reduce fixation time, etc.) and/or monitoring. In some protocols, a sample can be soaked in media to manage the effects of perfusion through the sample. If the sample is fixed using formalin, the sample can be pre-soaked in formalin to ensure sufficient diffusion of formalin into the inner sample regions without substantial amounts of cross-linking. FIG. 39 shows time versus a TOF signal for different tissue samples. The pre-soaked tissue sample was submersed in cold formalin at 4° C. for about 2 hours. The pre-soaked sample was then submerged in high temperature formalin bath (e.g., a bath of 10% NBF at about 45° C.) to cause cross-linking and accelerate the fixation process. The pre-soaked curve shows that the TOF signal gradually decreases as the sample is fixed. If the sample is processed with glycerol solution, the sample can be pre-soaked in glycerol solution or other type of media with characteristics similar to the characteristics of glycerol solution.

Pre-soaking minimizes, limits, or substantially eliminates the effects of water displacement that significantly changes the acoustic characteristics of the tissue sample. A comparison of the pre-soaked curve and the not pre-soaked curve shows that pre-soaking limits or substantially eliminates changes in TOF attributable to media perfusion causing displacement of lower density water in the tissue. The initial increase in phase comparison data for the not pre-soaked tissue may be caused by media perfusion (e.g., formalin perfusion) into the tissue, thereby displacing lower density water with higher density formalin (e.g., due to contained phosphates). The displacement phase is typically followed by the cross-linking phase, as indicated by rapidly declining or increasing TOF signal. A wide range of different types of fluid perfusion processes can be monitored because most processing media causes a density change in the sample.

Temperature changes in the tissue samples can affect TOF measurements. The samples can be at a temperature that is generally equal to the temperature of the media to minimize, limit, or substantially eliminate changes in TOF attributable to density changes caused by temperature changes. If the sample is at a different temperature than the temperature of the media, thermal equilibration can be accounted for because thermal equilibrium can be achieve within a few minutes after submersion in the warm solution. For example, if a sample at 4° C. is submerged in a warm formalin bath (e.g., a bath at 45° C.), the sample can reach thermal equilibrium in less than about five minutes. Based on the tissue size and characteristics (e.g., thermal characteristics), the time to reach thermal equilibrium can be estimated.

Figure 40:
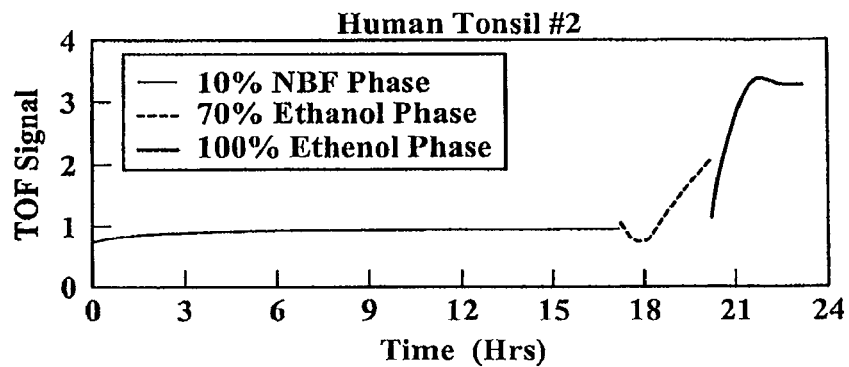
FIG. 40 is a plot of time versus a time of flight signal for a fixation and dehydration process.

Processes that cause changes to tissue structure can be monitored using the TOF measurements. For example, a dehydration process can cause measurable mechanical changes in the tissue. FIG. 40 shows time versus TOF signal for a human tonsil. The dehydration processing causes significant changes in TOF greater than the changes of TOF caused by fixation. Human tonsil was dehydrated using a 70% ethanol solution by volume and further dehydrated using a 100% ethanol solution by volume. The TOF signals shown in FIG. 40 were generated using phase detection algorithms covering multiple wavelengths.

In other dehydration protocols, tissue is exposed to gradated alcohol concentrations, to first remove phosphate buffers with a 70% ethanol/water mixture, followed by additional steps in 95% and 100% ethanol by volume to further dehydrate the fixed tissue. The tissue can undergo substantial shrinkage (e.g., more than 10% of its original volume). The amount of shrinkage can be determined using TOF measurements. The tissue shrinkage can be detected by TOF monitoring due to the resulting change in the tissue sample (e.g., tissue hardening, tissue shrinkage, etc.).

Figure 41:
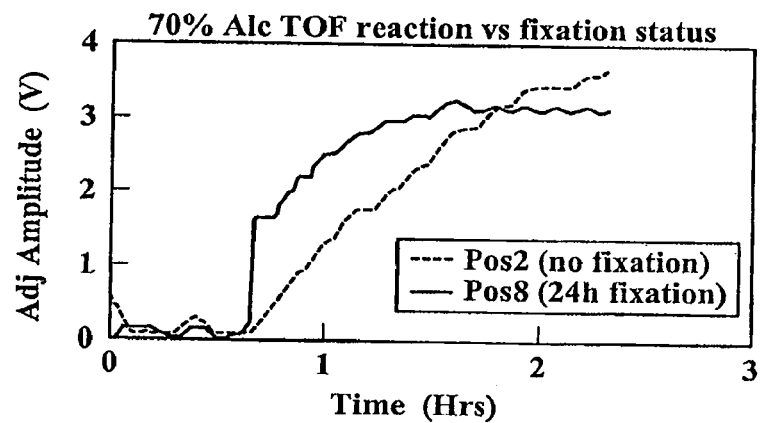
FIG. 41 is a plot of time versus amplitude of a time of flight signal for insufficiently fixed tissue and fixed tissue.

Monitoring can be used to evaluate whether samples are properly processed. FIG. 41 shows time versus TOF signals of an alcohol dehydration process. The alcohol dehydration can rely on sufficient cross-linking established during the fixation process. The resulting tissue compression during the dehydration processes can be empirically known to produce more disruptive tissue effects (such as tearing and cell and nucleus contraction) when the fixation step is omitted or too short. FIG. 41 shows differences in the TOF signal in 70% alcohol by volume of insufficiently fixed tissue versus properly fixed tissue. The overall process time of unfixed tissue in alcohol is significantly longer and the observed TOF changes are much larger than in fixed tissue (after 24 hours of standard fixation).

Figure 42:
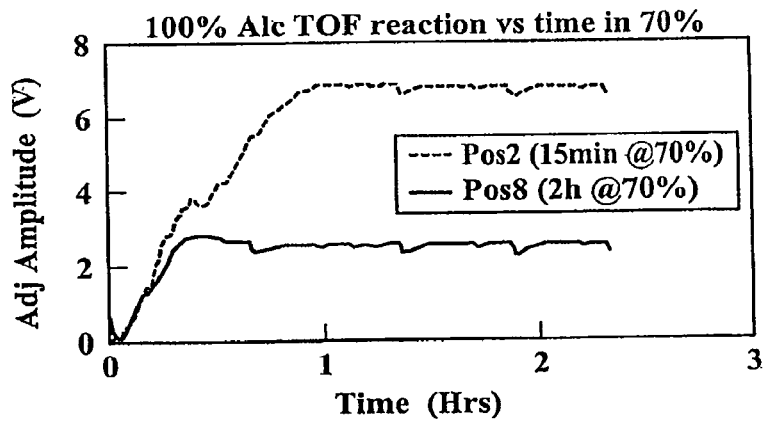
FIG. 42 is a plot of time versus time of flight signal amplitude for a tissue specimen submerged for different lengths of time in formalin.

Samples can be processed successively in different media to enhance TOF measurements. A first dehydration process can be performed in a preconditioning media. For example, a sample can be submerged in a bath of 70% alcohol by volume for about 15 minutes. The partially dehydrated sample is then subjected to a second dehydration process involving submerging the partial dehydrated sample in a bath of 100% alcohol by volume. As shown in FIG. 42, preconditioning produces a much larger TOF response in the 100% alcohol bath as compared to a sample processed in a bath of 70% alcohol for about 2 hours. The response in tissue compression is likely much higher when skipping or performing for too little time the 70% alcohol step.

Compensation protocols can be used to minimize, limit, or substantially eliminate unwanted noise cause by the environmental factors. The environmental factors may include, without limitation, temperature changes due to the ambient temperature, evaporative losses, media density changes (e.g., due to chemical reactions), or the like. If the temperature of the media fluctuates, the density of the media can also fluctuate and lead to noise in the TOF measurements. A thermal device (e.g., heating/cooling device) can keep the media within a desired temperature range or at a desired temperature. Additionally, a container holding the media can be thermally insulated to minimize or limit temperature changes.

The containers can be closed to avoid evaporative losses to minimize, limit, or substantially avoid drift. Evaporation of the media can result in a gradual change in TOF over time. For example, a total change in TOF of about 25 nanoseconds can result from about 15 hours of evaporation. Lids or covers can be placed on the containers to avoid or limit evaportaion. Alternatively or additionally, media can be pumped into a container to maintain a desired characteristic of the media.

Compensation schemes can be used to minimize, limit, or substantially eliminate environmental influences by using a reference channel (i.e., a position where data is taken, but the tissue or cassette is not in the way of the beam). Data values at this position can be subtracted from values at target positions.

A wide range of signal processing routines can be used to analyze the signals discussed herein. Filtering routines, compression routines (e.g., true pulse compression routines), cross-correlation routines, auto correlation signal recovery (especially in noisy environments), or the like can be utilized. Signal processing is especially well suited when samples are in relatively small containers in which there may be standing waves, reflections, and echoing. Signal processing routines can thus be selected to significantly improve signal-to-noise ratios.

It should be noted that, as used in this specification and the appended claims, the singular forms "a," "an," and "the" include plural referents unless the content clearly dictates otherwise. Thus, for example, reference to an analyzer including "a transmitter" includes a single transmitter, or two or more transmitters. It should also be noted that the term "or" is generally employed in its sense including "and/or" unless the content clearly dictates otherwise.

The various embodiments and features described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of processing a tissue sample comprising:
   (i) immersing the tissue sample in a fixative solution having a first temperature ranging from 0° C. to 10° C. for a first time period sufficient to diffuse the fixative solution into an interior region of the tissue sample without substantially forming cross-links within the tissue sample; and
   (ii) continuing immersion of the tissue sample in the fixative solution for a second period of time sufficient to cause cross-linking within the tissue sample,
   wherein the tissue sample is not exposed to ultrasonic or electromagnetic irradiation during either (i) the immersion of the tissue sample in the fixative solution, or (ii) the continuing immersion of the tissue sample in the fixative solution.

2. The method of claim 1, wherein the first time period is about 2 hours.

3. The method of claim 1, wherein the first temperature is about 4° C.

4. The method of claim 1, wherein the immersion in the fixative solution for the second period of time is continued by submerging the tissue sample in a warm fixative bath.

5. The method of claim 4, wherein the warm fixative bath has a temperature of about 45° C.

6. The method of claim 5, wherein the second time period is about 2 hours.

7. The method of claim 1, wherein the immersion in the fixative solution for the second time period is continued by heating the fixative solution from the first temperature to a second temperature.

8. The method of claim 1, wherein the fixative solution is 10% NBF.

9. The method of claim 1, wherein the second time period is about 2 hours.

10. The method of claim 1, wherein the second time period is about 4 hours.

11. The method of claim 1, wherein the second time period is about 6 hours.

12. The method of claim 1, where the first time period is sufficient to diffuse the fixative solution throughout substantially all of the tissue sample.

13. The method of claim 1, further comprising monitoring the diffusion of the fixative solution through the tissue sample.

14. The method of claim 1, wherein the monitoring comprises evaluating a change in a time of flight of acoustic waves that travel through the tissue sample while it is immersed within the fixative solution at the first temperature.

15. The method of claim 1, further comprising monitoring the cross-linking of the tissue sample.

* * * * *